(12) United States Patent
Vidlund et al.

(10) Patent No.: US 7,044,905 B2
(45) Date of Patent: May 16, 2006

(54) SPLINT ASSEMBLY FOR IMPROVING CARDIAC FUNCTION IN HEARTS, AND METHOD FOR IMPLANTING THE SPLINT ASSEMBLY

(75) Inventors: Robert Vidlund, Maplewood, MN (US); Thomas Paulson, Minneapolis, MN (US); Todd Mortier, Minneapolis, MN (US); Cyril Schweich, Jr., St. Paul, MN (US); Jeffrey LaPlante, Minneapolis, MN (US); David Kusz, Minneapolis, MN (US); Richard Schroeder, Fridley, MN (US)

(73) Assignee: Myocor, Inc., Maple Grove, MN (US)

( * ) Notice: Subject to any disclaimer, the term of this patent is extended or adjusted under 35 U.S.C. 154(b) by 630 days.

(21) Appl. No.: 10/278,847

(22) Filed: Oct. 24, 2002

(65) Prior Publication Data
US 2003/0050529 A1   Mar. 13, 2003

Related U.S. Application Data

(63) Continuation of application No. 09/532,049, filed on Mar. 21, 2000, now Pat. No. 6,537,198.

(51) Int. Cl.
*A61M 31/00* (2006.01)
*A61B 17/12* (2006.01)

(52) U.S. Cl. .......................................... 600/16; 600/37
(58) Field of Classification Search ............ 600/16–18, 600/37; 601/11; 623/3, 3.1, 904, 910; 128/898, 128/899
See application file for complete search history.

(56) References Cited

U.S. PATENT DOCUMENTS

| | | | |
|---|---|---|---|
| 4,192,293 A | 3/1980 | Asrican | |
| 4,261,342 A | 4/1981 | Aranguren Duo | |
| 4,372,293 A | 2/1983 | Vijil-Rosales | |

(Continued)

FOREIGN PATENT DOCUMENTS

DE   296 19 294   8/1987

(Continued)

OTHER PUBLICATIONS

Acorn Cardiovascular, Inc., "Acorn Cardiovascular Summary", undated.

(Continued)

*Primary Examiner*—Jeffrey R. Jastrzab
(74) *Attorney, Agent, or Firm*—Finnegan, Henderson, Farabow, Garrett & Dunner, L.L.P.

(57) ABSTRACT

A splint assembly for placement transverse a heart chamber to reduce the heart chamber radius and improve cardiac function has a tension member formed of a braided cable with a covering. A fixed anchor assembly is attached to one end of the tension member and a leader for penetrating a heart wall and guiding the tension member through the heart is attached to the other end. An adjustable anchor assembly can be secured onto the tension member opposite to the side on which the fixed pad assembly is attached. The adjustable anchor assembly can be positioned along the tension member so as to adjust the length of the tension member extending between the fixed and adjustable anchor assemblies. The pad assemblies engage with the outside of the heart wall to hold the tension member in place transverse the heart chamber. A probe and marker delivery device is used to identify locations on the heart wall to place the splint assembly such that it will not interfere with internal heart structures. The device delivers a marker to these locations on the heart wall for both visual and tactile identification during implantation of the splint assembly in the heart.

25 Claims, 13 Drawing Sheets

U.S. PATENT DOCUMENTS

| | | | |
|---|---|---|---|
| 4,409,974 A | 10/1983 | Freedland |
| 4,536,893 A | 8/1985 | Parravicini |
| 4,690,134 A | 9/1987 | Snyders |
| 4,705,040 A | 11/1987 | Mueller et al. |
| 4,936,857 A | 6/1990 | Kulik |
| 4,944,753 A | 7/1990 | Burgess et al. |
| 4,960,424 A | 10/1990 | Grooters |
| 4,997,431 A | 3/1991 | Isner et al. |
| 5,104,407 A | 4/1992 | Lam et al. |
| 5,106,386 A | 4/1992 | Isner et al. |
| 5,131,905 A | 7/1992 | Grooters |
| RE34,021 E | 8/1992 | Mueller et al. |
| 5,169,381 A | 12/1992 | Snyders |
| 5,192,314 A | 3/1993 | Daskalakis |
| 5,250,049 A | 10/1993 | Michael |
| 5,284,488 A | 2/1994 | Sideris |
| 5,385,528 A | 1/1995 | Wilk |
| 5,433,727 A | 7/1995 | Sideris |
| 5,450,860 A | 9/1995 | O'Connor |
| 5,452,733 A | 9/1995 | Sterman et al. |
| 5,458,574 A | 10/1995 | Machold et al. |
| 5,496,305 A | 3/1996 | Kittrell et al. |
| 5,509,428 A | 4/1996 | Dunlop |
| 5,533,958 A | 7/1996 | Wilk |
| 5,571,215 A | 11/1996 | Sterman et al. |
| 5,584,803 A | 12/1996 | Stevens et al. |
| 5,593,424 A | 1/1997 | Northrup III |
| 5,665,092 A | 9/1997 | Mangiardi et al. |
| 5,682,906 A | 11/1997 | Sterman et al. |
| 5,702,343 A | 12/1997 | Alferness |
| 5,713,954 A | 2/1998 | Rosenberg et al. |
| 5,718,725 A | 2/1998 | Sterman et al. |
| 5,755,783 A | 5/1998 | Stobie et al. |
| 5,758,663 A | 6/1998 | Wilk et al. |
| 5,800,334 A | 9/1998 | Wilk |
| 5,800,528 A | 9/1998 | Lederman et al. |
| 5,800,531 A | 9/1998 | Cosgrove et al. |
| 5,814,097 A | 9/1998 | Sterman et al. |
| 5,849,005 A | 12/1998 | Garrison et al. |
| 5,855,601 A | 1/1999 | Bessler et al. |
| 5,855,614 A | 1/1999 | Stevens et al. |
| 5,865,791 A | 2/1999 | Whayne et al. |
| 5,902,229 A | 5/1999 | Tsitlik et al. |
| 5,928,281 A | 7/1999 | Huynh et al. |
| 5,944,738 A | 8/1999 | Amplatz et al. |
| 5,957,977 A | 9/1999 | Melvin |
| 5,961,440 A | 10/1999 | Schweich, Jr. et al. |
| 5,961,549 A | 10/1999 | Nguyen et al. |
| 5,971,910 A | 10/1999 | Tsitlik et al. |
| 5,971,911 A | 10/1999 | Wilk |
| 5,972,022 A | 10/1999 | Huxel |
| 5,972,030 A | 10/1999 | Garrison et al. |
| 5,984,857 A | 11/1999 | Buck et al. |
| 5,984,917 A | 11/1999 | Fleischman et al. |
| 6,001,126 A | 12/1999 | Nguyen-Thien-Nhon |
| 6,024,096 A | 2/2000 | Buckberg |
| 6,024,756 A | 2/2000 | Huebsch et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,071,303 A | 6/2000 | Laufer |
| 6,077,214 A | 6/2000 | Mortier et al. |
| 6,077,218 A | 6/2000 | Alferness |
| 6,079,414 A | 6/2000 | Roth |
| 6,085,754 A | 7/2000 | Alferness et al. |
| 6,086,532 A | 7/2000 | Panescu et al. |
| 6,095,968 A | 8/2000 | Snyders |
| 6,102,944 A | 8/2000 | Huynh et al. |
| 6,110,100 A | 8/2000 | Talpade |
| 6,117,159 A | 9/2000 | Huebsch et al. |
| 6,123,662 A | 9/2000 | Alferness et al. |
| 6,125,852 A | 10/2000 | Stevens et al. |
| 6,126,590 A | 10/2000 | Alferness |
| 6,132,438 A | 10/2000 | Fleischman et al. |
| 6,143,025 A | 11/2000 | Stobie et al. |
| 6,155,968 A | 12/2000 | Wilk |
| 6,155,972 A | 12/2000 | Nauertz et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,121 A | 12/2000 | Alferness |
| 6,165,122 A | 12/2000 | Alferness |
| 6,165,183 A | 12/2000 | Kuehn et al. |
| 6,169,922 B1 | 1/2001 | Alferness et al. |
| 6,174,279 B1 | 1/2001 | Girard |
| 6,179,791 B1 | 1/2001 | Krueger |
| 6,182,664 B1 | 2/2001 | Cosgrove |
| 6,183,512 B1 | 2/2001 | Howanec, Jr. et al. |
| 6,190,408 B1 | 2/2001 | Melvin |
| 6,193,648 B1 | 2/2001 | Krueger |
| 6,197,053 B1 | 3/2001 | Cosgrove et al. |
| 6,206,820 B1 | 3/2001 | Kazi et al. |
| 6,210,432 B1 | 4/2001 | Solem et al. |
| 6,217,610 B1 | 4/2001 | Carpentier et al. |
| 6,221,013 B1 | 4/2001 | Panescu et al. |
| 6,221,103 B1 | 4/2001 | Melvin |
| 6,221,104 B1 | 4/2001 | Buckberg et al. |
| 6,224,540 B1 | 5/2001 | Lederman et al. |
| 6,230,714 B1 | 5/2001 | Alferness et al. |
| 6,231,561 B1 | 5/2001 | Frazier et al. |
| 6,231,602 B1 | 5/2001 | Carpentier et al. |
| 6,238,334 B1 | 5/2001 | Easterbrook, III et al. |
| 6,241,654 B1 | 6/2001 | Alferness |
| 6,245,102 B1 | 6/2001 | Jayaraman |
| 6,245,105 B1 | 6/2001 | Nguyen et al. |
| 6,250,308 B1 | 6/2001 | Cox |
| 6,251,061 B1 | 6/2001 | Hastings et al. |
| 6,258,021 B1 | 7/2001 | Wilk |
| 6,260,820 B1 | 7/2001 | Chowdhury |
| 6,261,222 B1 | 7/2001 | Schweich, Jr. et al. |
| 6,264,602 B1 | 7/2001 | Mortier et al. |
| 6,269,819 B1 | 8/2001 | Oz et al. |
| 6,283,993 B1 | 9/2001 | Cosgrove et al. |
| 6,290,674 B1 | 9/2001 | Roue et al. |
| 6,293,906 B1 | 9/2001 | Vanden Hoek et al. |
| 6,312,447 B1 | 11/2001 | Grimes |
| 6,314,322 B1 | 11/2001 | Rosenberg |
| 6,328,727 B1 | 12/2001 | Frazier et al. |
| 6,331,157 B1 | 12/2001 | Hancock |
| 6,332,863 B1 | 12/2001 | Schweich, Jr. et al. |
| 6,332,864 B1 | 12/2001 | Schweich, Jr. et al. |
| 6,332,893 B1 | 12/2001 | Mortier et al. |
| 6,343,605 B1 | 2/2002 | Lafontaine |
| 6,360,749 B1 | 3/2002 | Jayaraman |
| 6,370,429 B1 | 4/2002 | Alferness et al. |
| 6,375,608 B1 | 4/2002 | Alferness |
| 6,379,366 B1 | 4/2002 | Fleischman et al. |
| 6,402,679 B1 | 6/2002 | Mortier et al. |
| 6,402,680 B1 | 6/2002 | Mortier et al. |
| 6,402,781 B1 | 6/2002 | Langberg et al. |
| 6,406,420 B1 | 6/2002 | McCarthy et al. |
| 6,406,422 B1 | 6/2002 | Landesberg |
| 6,409,759 B1 | 6/2002 | Peredo |
| 6,409,760 B1 | 6/2002 | Melvin |
| 6,416,459 B1 | 7/2002 | Haindl |
| 6,419,669 B1 | 7/2002 | Frazier et al. |
| 6,432,039 B1 | 8/2002 | Wardle |
| 6,436,088 B1 | 8/2002 | Frazier et al. |
| 6,439,237 B1 | 8/2002 | Buckberg et al. |
| 6,450,171 B1 | 9/2002 | Buckberg et al. |
| 6,494,825 B1 | 12/2002 | Talpade |
| 2001/0003986 A1 | 6/2001 | Cosgrove |
| 2001/0005787 A1 | 6/2001 | Oz et al. |
| 2001/0009976 A1 | 7/2001 | Panescu et al. |

| | | | |
|---|---|---|---|
| 2001/0014800 A1 | 8/2001 | Frazier et al. | |
| 2001/0014811 A1 | 8/2001 | Hussien | |
| 2001/0018611 A1 | 8/2001 | Solem et al. | |
| 2001/0021874 A1 | 9/2001 | Carpentier et al. | |
| 2001/0029314 A1 | 10/2001 | Alferness et al. | |
| 2001/0034551 A1 | 10/2001 | Cox | |
| 2001/0037123 A1 | 11/2001 | Hancock | |
| 2001/0039434 A1 | 11/2001 | Frazier et al. | |
| 2001/0039435 A1 | 11/2001 | Roue et al. | |
| 2001/0039436 A1 | 11/2001 | Frazier et al. | |
| 2001/0041821 A1 | 11/2001 | Wilk | |
| 2001/0041914 A1 | 11/2001 | Frazier et al. | |
| 2001/0041915 A1 | 11/2001 | Roue et al. | |
| 2001/0044568 A1 | 11/2001 | Langberg et al. | |
| 2001/0047122 A1 | 11/2001 | Vanden Hoek et al. | |
| 2001/0049492 A1 | 12/2001 | Frazier et al. | |
| 2002/0007216 A1 | 1/2002 | Melvin | |
| 2002/0013571 A1 | 1/2002 | Goldfarb et al. | |
| 2002/0016628 A1 | 2/2002 | Langberg et al. | |
| 2002/0019580 A1 | 2/2002 | Lau et al. | |
| 2002/0022880 A1 | 2/2002 | Melvin | |
| 2002/0026092 A1 | 2/2002 | Buckberg et al. | |
| 2002/0028981 A1 | 3/2002 | Lau et al. | |
| 2002/0029783 A1 | 3/2002 | Stevens et al. | |
| 2002/0032364 A1 | 3/2002 | Lau et al. | |
| 2002/0045798 A1 | 4/2002 | Lau et al. | |
| 2002/0045799 A1 | 4/2002 | Lau et al. | |
| 2002/0045800 A1 | 4/2002 | Lau et al. | |
| 2002/0052538 A1 | 5/2002 | Lau et al. | |
| 2002/0056461 A1 | 5/2002 | Jayaraman | |
| 2002/0058855 A1 | 5/2002 | Schweich, Jr. et al. | |
| 2002/0065449 A1 | 5/2002 | Wardle | |
| 2002/0077532 A1 | 6/2002 | Gannoe et al. | |
| 2002/0091296 A1 | 7/2002 | Alferness | |
| 2002/0103511 A1 | 8/2002 | Alferness et al. | |
| 2002/0111533 A1 | 8/2002 | Melvin | |
| 2002/0111636 A1 | 8/2002 | Fleischman et al. | |
| 2002/0133055 A1 | 9/2002 | Haindl | |
| 2002/0161275 A1 | 10/2002 | Schweich, Jr. et al. | |
| 2002/0169358 A1 | 11/2002 | Mortier et al. | |
| 2002/0169359 A1 | 11/2002 | McCarthy et al. | |
| 2002/0173694 A1 | 11/2002 | Mortier et al. | |

FOREIGN PATENT DOCUMENTS

| | | |
|---|---|---|
| DE | 36 14 292 | 11/1987 |
| DE | 42 34 127 | 5/1994 |
| DE | 199 47 885 | 4/2000 |
| EP | 0 583 012 | 2/1994 |
| EP | 0 820 729 A1 | 1/1998 |
| EP | 1 129 736 A1 | 9/2001 |
| WO | 91/19465 | 12/1991 |
| WO | 95/06447 | 3/1995 |
| WO | 95/16476 | 6/1995 |
| WO | 96/04852 | 2/1996 |
| WO | 96/40356 | 12/1996 |
| WO | WO 97/14286 | 4/1997 |
| WO | 97/24082 | 7/1997 |
| WO | 97/24083 | 7/1997 |
| WO | 97/24101 | 7/1997 |
| WO | 98/03213 | 1/1998 |
| WO | 98/14136 | 4/1998 |
| WO | WO 98/17347 | 4/1998 |
| WO | 98/18393 | 5/1998 |
| WO | 98/26738 | 6/1998 |
| WO | 98/29041 | 7/1998 |
| WO | 98/32382 | 7/1998 |
| WO | WO 98/58598 | 12/1998 |
| WO | 99/00059 | 1/1999 |
| WO | 99/11201 | 3/1999 |
| WO | 99/13777 | 3/1999 |
| WO | 99/30647 | 6/1999 |
| WO | 99/44534 | 9/1999 |
| WO | 99/44680 | 9/1999 |
| WO | 99/52470 | 10/1999 |
| WO | 99/56655 | 11/1999 |
| WO | 00/02500 | 1/2000 |
| WO | 00/03759 | 1/2000 |
| WO | 00/06026 | 2/2000 |
| WO | 00/06028 | 2/2000 |
| WO | 00/13722 | 3/2000 |
| WO | 00/18320 | 4/2000 |
| WO | 00/27304 | 5/2000 |
| WO | 00/28912 | 5/2000 |
| WO | 00/28918 | 5/2000 |
| WO | WO 00/25842 | 5/2000 |
| WO | 00/36995 | 6/2000 |
| WO | 00/42919 | 7/2000 |
| WO | 00/42950 | 7/2000 |
| WO | 00/42951 | 7/2000 |
| WO | 00/45735 | 8/2000 |
| WO | 00/60995 | 10/2000 |
| WO | 00/61033 | 10/2000 |
| WO | 00/62715 | 10/2000 |
| WO | 00/62727 | 10/2000 |
| WO | 01/00111 | 1/2001 |
| WO | 01/03608 | 1/2001 |
| WO | 01/19291 | 3/2001 |
| WO | 01/19292 | 3/2001 |
| WO | 01/21070 | 3/2001 |
| WO | 01/21098 | 3/2001 |
| WO | 01/21099 | 3/2001 |
| WO | 01/26557 | 4/2001 |
| WO | 01/28432 | 4/2001 |
| WO | 01/50981 | 7/2001 |
| WO | WO 01/49217 A2 | 7/2001 |
| WO | 01/54618 | 8/2001 |
| WO | 01/54745 | 8/2001 |
| WO | WO 01/54562 A2 | 8/2001 |
| WO | 01/67985 | 9/2001 |
| WO | 01/91667 | 12/2001 |
| WO | 01/95830 | 12/2001 |
| WO | 01/95831 | 12/2001 |
| WO | 01/95832 | 12/2001 |

OTHER PUBLICATIONS

Acorn Cardiovascular, Inc., "Acorn Cardiovasculer Company Overview", undated.
Acorn Cardiovascular Highlights, Abstracts, Mar. 10, 1999.
Acorn Cardiovascular Highlights, Abstracts, Apr. 19, 1999.
Acorn Cardiovascular Highlights, Abstracts, Oct. 1, 1999.
Acorn Cardiovascular Highlights, Abstracts, Nov. 9, 1999.
Batista, MD et al., "Partial Left Ventriculectomy to Treat End-Stage Heart Disease", *Ann. Thorac. Surg.*, 64:634-8, 1997.
Melvin, DB, "Ventricular Radius-Reduction Without Resection, A Computational Assessment", undated.
Melvin, DB et al., "Reduction of Ventricular Wall Tensile Stress by Geometric Remodeling Device,"Poster Text, ASAIO, 1999.
Kay et al., "Surgical Treatment of Mitral Insufficiency", *The Journal of Thoracic Surgery*, 29: 618-620, 1955.
Harken et al., "The Surgical Correction of Mitral Insufficiency", *The Journal of Thoracic Surgery*, 28:604-627, 1954.
Bailey et al., "Closed Intracardiac Tactile Surgery", *Diseases of the Chest*, XXII:1-24, Jul. 1952.
Sakakibara, "A Surgical Approach to the Correction of Mitral Insufficiency", *Annals of Surgery*, 142:196-203, 1955.
Glenn et al., "The Surgical Treatment of Mitral Insufficiency: The Fate of A Vascularized Transchamber Intracardiac Graft", *Annals of Surgery*, 141:510-518, Apr. 1955.

Kay et al., "Surgical Treatment of Mitral Insufficiency", *Surgery*, 37:697-706, May 1955.

Bailey et al. The Surgical Correction of Mitral Insufficiency By The Use of Pericardial Grafts, *The Journal of Thoracic Surgery*, 28:551-603, Dec. 1954.

Harken et al., "The Surgical Correction of Mitral Insufficiency", Surgical forum, 4:4-7, 1953.

Shumacker, Jr., "Attempts to Control Mitral Regurgitation", *The Evolution of Cardiac Surgery*, 203-210, 1992.

Edie, M.D. et al., "Surgical repair of single ventricle,"*The Journal of Thoracic and Cardiovascular Surgery*, vol. 66, No. 3, Sep., 1973, pp. 350-360.

McGoon, M.D. et al., "Correction of the univentricular heart having two atrioventricular valves," *The Journal of Thoracic and Cardiovascular Surgery*, vol. 74, No. 2, Aug., 1977, pp. 218-226.

Lev, M.D., et al., "Single (Primitive) Ventricle," *Circulation*, vol. 39, May, 1969, pp. 577-591.

Westaby with Bosher, "Landmarks in Cardiac Surgery," 1997, pp. 198-199.

Shumacker, "Cardiac Aneurysms," *The Evolution of Cardiac Surgery*, 1992, pp. 159-165.

Feldt, M.D., "Current status of the septation procedure for univentricular heart," *The Journal Thoracic and Cardiovascular Surgery*, vol. 82, No. 1, Jul., 1981, pp. 93-97.

Doty, M.D., "Septation of the univentricular heart," *The Journal of Thoracic and Cardiovascular Surgery*, vol. 78, No. 3, Sep., 1979, pp. 423-430.

Carpentier et al., "Myocardial Substitution with a Stimulated Skeletal Muscle: First Successful Clinical Case," Letter to the Editor, p. 1267, Sep. 25, 1996.

Ianuzzo et al., "Preservation of the Latissimus Dorsi Muscle During Cardiomyoplasty Surgery," *J. Card. Surg.*, 1996:11:99-108.

Ianuzzo et al., "On Preconditioning of Skeletal Muscle: Application to Dynamic Cardiomyoplasty," Invited Commentary, *J. Card. Surg.*, 1996:11:109-110.

Chachques et al., "Latissimus Dorsi Dynamic Cardiomyoplasty," *Ann. Thorac. Surg.*, 1989:47:600-604.

Moreira et al., "Latissimus Dorsi Cardiomyoplasty in the Treatment of Patients with Dilated Cardiomyopathy," Supplement IV Circulation, Sep. 25, 1996, 7 pgs.

Lucas et al., "Long-Term Follow-Up (12 to 35 Weeks) After Dynamic Cardiomyoplasty," *JACC*, vol. 22, No. 3, Sep. 1993:758-67.

Batista et al., "Partial Left Ventriculectomy to Improve Left Ventricular Function in End-Stage Heart Disease," *J. Card. Surg.*, 1996:11:96-98.

"Congestive Heart Failure in the United States: A New Epidemic" Data Fact Sheet, National Heart, Lung, and Blood Institute, National Institutes of Health, Dec. 9, 1996, pp. 1-6.

Kormos et al., "Experience with Univentricular Support in Mortally III Cardiac Transplant Candidates," *Ann. Thorac. Surg.*, 1990:49:261-71.

Wampler et al., "Treatment of Cardiogenic Shock with the Hemopump Left Ventricular Assist Device," *Ann. Thorac. Surg.*, 1991:52:506-13.

McCarthy et al., "Clinical Experience with the Novacor Ventricular Assist System," *J. Thorac. Cardiovasc. Surg.*, 1991:102-578-87.

Burnett et al., "Improved Survival After Hemopump Insertion in Patients Experiencing Postcardiotomy Cardiogenic Shock During Cardiopulmonary Bypass," From the Section of Transplantation, Division of Cardiovascular Surgery, Texas Heart Institute and St. Luke's Episcopal Hospital, Houston, Texas, dated even with or prior to Jan. 2, 1997, pp. 626-628.

Phillips et al., "Hemopump Support for the Failing Heart," From the Department of Cardiovascular Medicine and Surgery, Mercy Hospital Medical Center, Des Moines, Iowa, date even with or prior to Jan. 2, 1997, pp. 629-631.

Deeb et al., "Clinical Experience with the Nimbus Pump," From the University of Michigan Medical Center Section of Thoracic Surgery and Division of Cardiology, Ann Arbor, Michigan, date even with or prior to Jan. 2, 1997, pp. 632-636.

Bearnson et al., "Development of a Prototype Magnetically Suspended Rotor Ventricular Assist Device," *ASAIO Journal*, 1996, pp. 275-280.

Sakakibara et al., "A Muscle Powered Cardiac Assist Device for Right Ventricular Support: Total Assist or Partial Assist?," *Trans. Am.Soc. Artif. Intern. Organs*, vol. XXXVI, 1990, pp. 372-375.

Medtronic, Inc. 1996 Annual Shareholders Report, 79 pages.

ABIOMED, Inc. Annual Report 1996, 32 pages.

Press Release dated Sep. 16, 1996, "ABIOMED Wins $8.5 Million Federal Contract to Qualify its Artificial Heart for Human Trials," 5 pages.

Press Release dated Sep. 26, 1996, ABIOMED's Temporary Artificial Heart System Reaches 200 U.S. Medical Center Milestone, 1 page.

Press Release dated May 17, 1996, "ABIOMED Receives FDA Approval to Expand Indications for Use of Cardiac Assist System," 1 page.

Press Release dated Oct. 3, 1995, "ABIOMED Wins $4.35 Million Contract from the National Heart, Lung and Blood Institutes to Develop Implantable Heart Booster," 1 page.

Press Release dated Sep. 29, 1995, "ABIOMED" Wins NIH Grant to Develop Calcification-Resistant Plastic Heart Valve, 1 page.

Press Release dated Aug. 25, 1995, "ABIOMED Wins Research Grant from NIH to Develop Suturing Instrument for Abdominal surgery," 1 page.

Press Release dated Aug. 11, 1995, "ABIOMED Receives Grant from NIH to Develop Disposable Bearingless Centrifugal Blood Pump," 1 page.

Press Release dated Jun. 9, 1995, "ABIOMED Receives Grant from National Institutes of Health to Develop a Laser Welding Technique for Tissue Repair," 1 page.

Press Release dated Apr. 27, 1995, "ABIOMED's Temporary Artificial Heart System Reaches 1,000 Patient Milestone; BVS-5000 in More Than 100 U.S. Medical Centers," 1 page.

"Reversible Cardiomyopathy," *Thoratec's Heartbeat*, vol. 10.2, Aug. 1996, 4 pages.

Tsai et al., "Surface Modifying Additives for Improved Device-Blood Compatibility," *ASAIO Journal*, 1994, pp. 619-624.

Farrar et al., "A New Skeletal Muscle Linear-Pull Energy Convertor as a Power Source for Prosthetic Support Devices," *The Journal of Heart & Lung Transplantation*, vol. 11, No. 5, Sep., 1992, pp. 341-349.

Brochure entitled "Thoratec Ventricular Assist Device System—Because Heart Patients Come in All Sizes," date even with or prior to Jan. 2, 1997, 5 pages.

Press Release dated Oct. 3, 1994, "Heartmate System Becomes First Implantable Cardiac-Assist Device to be Approved for Commercial Sale in the U.S.," 2 pages.

Bocchi et al., "Clinical Outcome after Surgical Remodeling of Left Ventricle in Candidates to Heart Transplantation with Idiopathic Dilated Cardiomypathy—Short Term Results," date even with or prior to Jan. 2, 1997, 1 page.

Bach et al., "Early Improvement in Congestive Heart Failure after Correction of Secondary Mitral Regurgitation in End-Stage Cardiomyopathy," *American Heart Journal*, Jun. 1995, pp. 1165-1170.

Schuler et al., "Temporal Response of Left Ventricular Performance to Mitral Valve Surgery," vol. 59, No. 6, Jun. 1979, pp. 1218-1231.

Huikuri, "Effect of Mitral Valve Replacement on Left Ventricular Function in Mitral Regurgitation," *Br. Heart J.*, vol. 49, 1983, pp. 328-333.

Pitarys II et al., "Long-Term Effects of Excision of the Mitral Apparatus on Global and Regional Ventricular Function in Humans," *JACC*, vol. 15, No. 3, Mar. 1, 1990, pp. 557-563.

Bolling et al., "Surgery for Acquired Heart Disease/Early Outcome of Mitral Valve Reconstruction in Patients with End-Stage Cardiomyopathy," *The Journal of Thoracic and Cardiovascular Surgery*, vol. 109, No. 4, Apr. 1995, pp. 676-683.

Masahiro et al., "Surgery for Acquired Heart Disease/Effects of Preserving Mitral Apparatus on Ventricular Systolic Function in Mitral Valve Operations in Dogs," *The Journal of Thoracic and Cardiovascular Surgery*, vol. 106, No. 6, Dec. 1993, pp. 1138-1146.

Dickstein et al., "Heart Reduction Surgery: An Analysis of the Impact on Cardiac Function," *The Journal of Thoracic and Cardiovascular Surgery*, vol. 113, No. 6, Jun. 1997, 9 pages.

McCarthy et al., "Early Results with Partial Left Ventriculectomy," From the Departments of Thoracic and Cardiovascular Surgery, Cardiology, and Transplant Center, Cleveland Clinic Foundation, Presented at the 77th Annual Meeting of the American Association of Thoracic Surgeons, May 1997, 33 pages.

Alonso-Lej, M.D., "Adjustable Annuloplasty for Tricuspid Insufficiency," *The Annals of Thoracic Surgery*, vol. 46, No. 3, Sep. 1988, 2 pages.

Kurlansky et al., "Adjustable Annuloplasty for Tricuspid Insufficiency," *Ann. Thorac. Surg.*, 44:404-406, Oct. 1987.

Savage, M.D., "Repair of left ventricular aneurysm," *The Journal of Thoracic and Cardiovascular Surgery*, vol. 104, No. 3, Sep., 1992, pp. 752-762.

Melvin, "Ventricular Radius Reduction Without Restriction: A Computational Analysis," *ASAIO Journal*, 45:160-165, 1999.

Cox, "Left Ventricular Aneurysms: Pathophysiologic Observations and Standard Resection," *Seminars in Thoracic and Cardiovascular Surgery*, vol. 9, No. 2, Apr., 1997, pp. 113-122.

Boyd et al., "Tricuspid Annuloplasty," *The Journal of Thoracic Cardiovascular Surgery*, vol. 68, No. 3, Sep. 1974, 8 pages.

"Heart 'jacket' could help stop heart failure progression," *Clinica*, 916, Jul. 10, 2000.

McCarthy et al., "Device Based Left Ventricular Shape Change Immediately Reduces Left Ventricular Volume and Increases Ejction Fraction in a Pacing Induced Cardiomyopathy Model in Dogs: A Pilot Study," *JACC*, Feb. 2000.

Melvin, DB et al., "Reduction of Ventricular Wall Tensile Stress by Geometric Remodeling Device," (1 page), undated.

McCarthy, Transscription of Mar. 13, 2000 Presentation, pp. 1-9.

US 6,197,052, 03/2001, Cosgrove et al. (withdrawn)

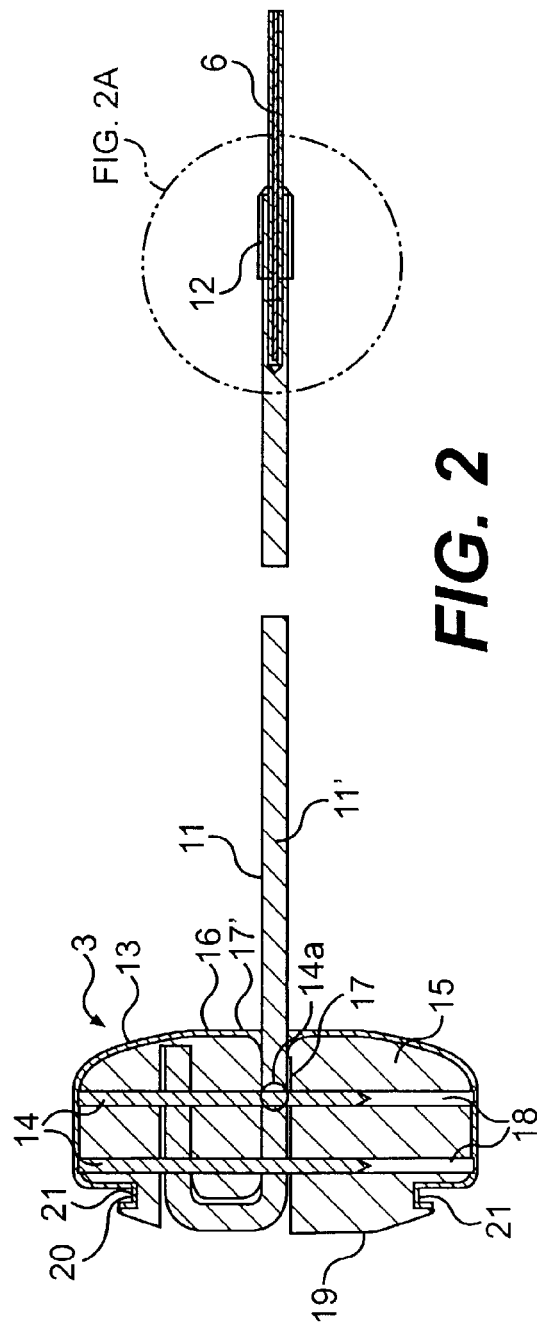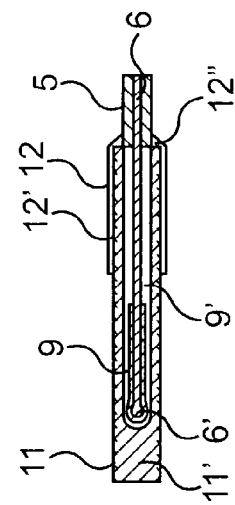

SPLINT ASSEMBLY FOR IMPROVING CARDIAC FUNCTION IN HEARTS, AND METHOD FOR IMPLANTING THE SPLINT ASSEMBLY

This application is a continuation of U.S. application Ser. No. 09/532,049, filed Mar. 21, 2000, now U.S. Pat. No. 6,537,198, which is incorporated herein by reference.

FIELD OF THE INVENTION

The present invention pertains to a device, and a method for placing the device, for treating a failing heart. In particular, the device and its related method of the present invention are directed toward reducing the wall stress in a failing heart. The device reduces the radius of curvature and/or alters the geometry or shape of the heart to thereby reduce wall stress in the heart and improve the heart's pumping performance.

BACKGROUND OF THE INVENTION

Heart failure is a common course for the progression of many forms of heart disease. Heart failure may be considered as the condition in which an abnormality of cardiac function is responsible for the inability of the heart to pump blood at a rate commensurate with the requirements of the metabolizing tissues, or can do so only at an abnormally elevated filling pressure. There are many specific disease processes that can lead to heart failure. Typically these processes result in dilatation of the left ventricular chamber. Etiologies that can lead to this form of failure include idiopathic, valvular, viral, and ischemic cardiomyopathies.

The process of ventricular dilatation is generally the result of chronic volume overload or specific damage to the myocardium. In a normal heart that is exposed to long term increased cardiac output requirements, for example, that of an athlete, there is an adaptive process of slight ventricular dilation and muscle myocyte hypertrophy. In this way, the heart fully compensates for the increased cardiac output requirements. With damage to the myocardium or chronic volume overload, however, there are increased requirements put on the contracting myocardium to such a level that this compensated state is never achieved and the heart continues to dilate.

The basic problem with a large dilated left ventricle is that there is a significant increase in wall tension and/or stress both during diastolic filling and during systolic contraction. In a normal heart, the adaptation of muscle hypertrophy (thickening) and ventricular dilatation maintain a fairly constant wall tension for systolic contraction. However, in a failing heart, the ongoing dilatation is greater than the hypertrophy and the result is a rising wall tension requirement for systolic contraction. This is felt to be an ongoing insult to the muscle myocyte resulting in further muscle damage. The increase in wall stress also occurs during diastolic filling. Additionally, because of the lack of cardiac output, a rise in ventricular filling pressure generally results from several physiologic mechanisms. Moreover, in diastole there is both a diameter increase and a pressure increase over normal, both contributing to higher wall stress levels. The increase in diastolic wall stress is felt to be the primary contributor to ongoing dilatation of the chamber. Prior treatments for heart failure associated with such dilatation fall into three general categories. The first being pharmacological, for example, diuretics and ACE inhibitors. The second being assist systems, for example, pumps. Finally, surgical treatments have been experimented with, which are described in more detail below.

With respect to pharmacological treatments, diuretics have been used to reduce the workload of the heart by reducing blood volume and preload. Clinically, preload is defined in several ways including left ventricular end diastolic pressure (LVEDP), or indirectly by left ventricular end diastolic volume (LVEDV). Physiologically, the preferred definition is the length of stretch of the sarcomere at end diastole. Diuretics reduce extra cellular fluid which builds in congestive heart failure patients increasing preload conditions. Nitrates, arteriolar vasodilators, angiotensin converting enzyme (ACE) inhibitors have been used to treat heart failure through the reduction of cardiac workload by reducing afterload. Afterload may be defined as the tension or stress required in the wall of the ventricle during ejection. Inotropes function to in-crease cardiac output by increasing the force and speed of cardiac muscle contraction. These drug therapies offer some beneficial effects but do not stop the progression of the disease.

Assist devices include mechanical pumps. Mechanical pumps reduce the load on the heart by performing all or part of the pumping function normally done by the heart. Currently, mechanical pumps are used to sustain the patient while a donor heart for transplantation becomes available for the patient.

There are at least three surgical procedures for treatment of heart failure associated with dilatation: 1) heart transplantation; 2) dynamic cardiomyoplasty; and 3) the Batista partial left ventriculectomy; and 4) the Jatene and Dor procedures for ischemic cardiomyopathy, discussed in more detail below. Heart transplantation has serious limitations including restricted availability of organs and adverse effects of immunosuppressive therapies required following heart transplantation. Cardiomyoplasty involves wrapping the heart with skeletal muscle and electrically stimulating the muscle to contract synchronously with the heart in order to help the pumping function of the heart. The Batista partial left ventriculectomy surgically remodels the left ventricle by removing a segment of the muscular wall. This procedure reduces the diameter of the dilated heart, which in turn reduces the loading of the heart. However, this extremely invasive procedure reduces muscle mass of the heart.

Another form of heart failure results from the formation of one or more zones of ischemia, or infarction, of the myocardium. Infarction occurs when blood supply to the heart tissue has been obstructed resulting in a region of tissue that loses its ability to contract (referred to as infarcted tissue). The presence of infarcted tissue may lead to three conditions in the heart causing cardiac malfunction. These conditions are ventricular aneurysms (ventricular dyskinesia), non-aneurysmal ischemic or infarcted myocardium (ventricular akinesia), and mitral regurgitation.

A ventricular aneurysm is formed when the infarction weakens the heart wall to such an extent that the tissue stretches and thins, causing, for example, the left ventricular wall to expand during systole (dyskinesia) and form a bulge in the heart wall. Non-aneurysmal ischemic or infarcted myocardium (akinesia) occurs when a major coronary artery is occluded and results in infarction in the myocardial tissue, but without a bulging aneurysm. Finally, mitral regurgitation is a condition whereby blood leaks through the mitral valve due to an improper positioning of the valve structures that causes it not to close entirely. If the infarcted or aneurysmal region is located in the vicinity of the mitral valve, geometric abnormalities may cause the mitral valve to alter its normal position and dimension, and may lead to annular dilatation and the development of mitral regurgitation.

The "Dor" and "Jatene" procedures have recently been employed to treat heart conditions resulting from aneurysms and other infarctions. In the "Dor" procedure, the aneurysm is removed and an endocardial patch is placed to cover the dyskinetic septal wall portion of the aneurysm. In this manner, at least the portion of stroke volume "lost" to dyskinesia is restored. In the "Jatene" technique, a purse string suture is placed at the base of the aneurysm. The infarcted septal wall is circumferentially reduced by inbrication with sutures.

SUMMARY OF THE INVENTION

The advantages and purpose of the invention will be set forth in part in the description which follows, and in part will be obvious from the description, or may be learned by practice of the invention. The advantages and purpose of the invention will be realized and attained by means of the elements and combinations particularly pointed out in the appended claims.

Due to the drawbacks and limitations of the previous devices and techniques for treating a failing heart, including such a heart having dilated, infarcted, and/or aneurysmal tissue, there exists a need for alternative methods and devices that are less invasive, pose less risk to the patient, and are likely to prove more clinically effective. The present invention provides such methods and devices.

Although throughout this specification, the inventive devices and methods will be discussed in connection with treating dilated heart chambers, it is contemplated that the form of heart failure resulting from aneurysms and the like also can be treated with the inventive device and method for using the device disclosed herein. U.S. application Ser. No. 09/422,328, filed on Oct. 21, 1999, entitled "Methods and Devices for Improving Cardiac Function in Hearts," which is assigned to the same assignee as the present application and is incorporated by reference herein, discusses this form of heart failure in more detail.

One aspect of the present invention pertains to a non-pharmacological, passive apparatus and method for the treatment of a failing heart due to dilatation. The device is configured to reduce the tension in the heart wall, and thereby reverse, stop or slow the disease process of a failing heart as it reduces the energy consumption of the failing heart, decreases isovolumetric contraction, increases isotonic contraction (sarcomere shortening), which in turn increases stroke volume.

The device reduces wall tension by changing chamber geometry or shape and/or changing the radius of curvature or cross-section of a heart chamber. These changes may occur during the entire cardiac cycle. The apparatuses of the present invention which reduce heart wall stress in this way can be referred to generally as "splints." Splints can be grouped as either "full cycle splints," which engage the heart to produce these changes throughout the cardiac cycle, or "restrictive splints," which engage the heart wall for only a portion of the cardiac cycle to produce these changes.

One aspect of the present invention includes an apparatus for improving cardiac function includes an elongate member configured to extend transverse a heart chamber, a first heart-engaging assembly attached to one end of the elongate member and configured to engage a first exterior location of a heart wall, and a second heart-engaging assembly configured to be secured onto the elongate member and to engage a second exterior location of the heart wall. The apparatus further includes a fixation member configured to penetrate the elongate member to thereby hold at least one of the first and second heart-engaging assemblies in a fixed position along the length of the elongate member.

According to another aspect of the present invention, an apparatus for improving cardiac function includes an elongate member configured to extend transverse a heart chamber, wherein the elongate member is made of a plurality of filament bundles of approximately 180 denier. The apparatus further includes a first heart-engaging assembly attached to one end of the elongate member and configured to engage a first exterior location of a heart wall and a second heart-engaging assembly configured to be secured onto the elongate member and to engage a second exterior location of the heart wall.

According to yet another aspect of the present invention an apparatus for improving cardiac function includes an elongate member attached to a leader member at one end thereof and being configured to extend transverse a heart chamber, a first heart-engaging assembly attached to the other end of the elongate member and configured to engage a first exterior location of a heart wall, and a second heart-engaging assembly configured to slidably receive the leader member and the elongate member and to thereby be secured to the elongate member and to engage a second exterior location of the heart wall The second heart-engaging assembly is configured to be secured to the elongate member such that a length of the elongate member between the first and second heart-engaging assemblies can be adjusted during placement of the elongate member transverse the heart chamber.

Another embodiment of the present invention includes an apparatus is provided for determining and marking locations on a heart wall. The apparatus includes a marker delivery mechanism configured to hold a marker and an actuator operatively connected to the marker delivery mechanism for delivering a marker to the location. The distal end of the delivery mechanism is configured to be visible relative to internal heart structures.

Yet another embodiment of the present invention includes a tool for fixing an elongate member to a housing comprising an engagement member configured to engage a fixation member to be advanced within the housing, a wire having a first end secured to the engagement member and being configured to pass through the housing, and a handle connected to a second end of the wire. The engagement member and the wire are further configured to move through the housing to advance the fixation member within the housing and into engagement with the elongate member when the handle is actuated.

In another embodiment of the present invention, there is provided a method for placing a splint assembly transverse a heart chamber. The method includes providing an elongate member with a leader member attached to a first end and a first heart-engaging assembly attached to a second end and guiding the leader member through first and second exterior locations on a heart wall so as to extend the elongate member transverse to the heart chamber. The method further includes adjusting the length of the elongate member extending through the heart chamber by securing a second heart-engaging assembly to the elongate member at a position along the length of the elongate member exterior the chamber at the second location.

In accordance with the purposes of the invention as embodied and broadly described herein, instruments and related methods for implanting the device for treating a heart and improving cardiac function also are disclosed.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and, together with the description, serve to explain the principles of the invention. In the drawings.

FIG. 2 is a cross-sectional view of a leader tube and a portion of the splint assembly showing the connection of a fixed pad assembly to the tension member;

FIG. 2A is a detailed view of section A—A of FIG. 2 showing the connection of the leader tube to the tension member;

FIG. 10A is a perspective view of the probe tip in FIG. 10 looking down onto the probe tip;

DESCRIPTION OF THE PREFERRED EMBODIMENTS

Figure 1:
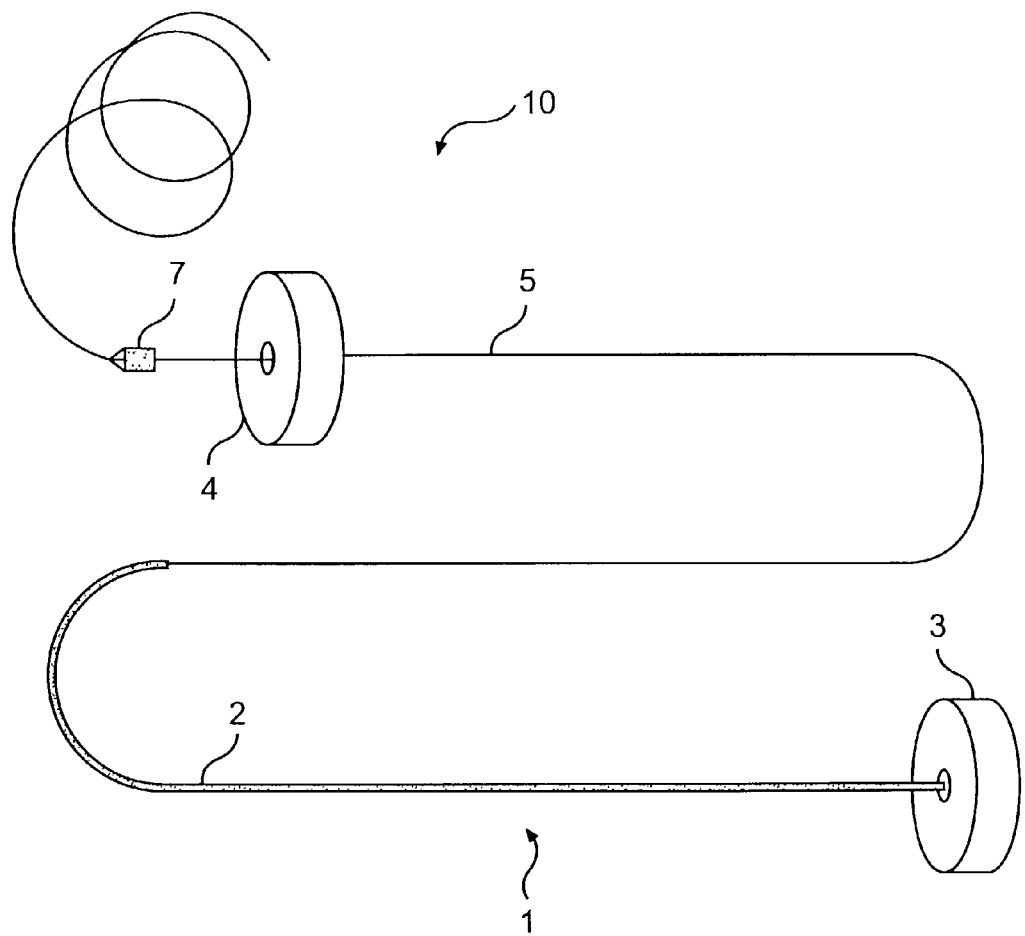
FIG. 1 is a plan view of an embodiment of the splint assembly and leader assembly according to the present invention.

The various aspects of the invention to be discussed herein generally pertain to devices and methods for treating heart conditions, including, for example, dilatation and other similar heart failure conditions. The device of the present invention preferably operates passively in that, once placed in the heart, it does not require an active stimulus, either mechanical, electrical, or otherwise, to function. Implanting one or more of these devices alters the shape or geometry of the heart, both locally and globally, and thereby increases the heart's efficiency. That is, the heart experiences an increased pumping efficiency through an alteration in its shape or geometry and concomitant reduction in stress on the heart walls.

Although the implanted device for treating the heart preferably is a passive device, it is contemplated that the inventive tools and instruments used for implanting the device and the method of using these tools and instruments can be used to implant other treatment devices, such as active devices and the like.

The inventive device and methods offer numerous advantages over the existing treatments for various heart conditions. The device is relatively easy to manufacture and use, and the related inventive surgical techniques and tools for implanting the device do not require the invasive procedures of current surgical techniques. For instance, the surgical technique does not require removing portions of the heart tissue, nor does it necessarily require opening the heart chamber or stopping the heart during operation. For these reasons, the surgical techniques of the present invention also are less risky to the patient than other techniques.

The disclosed inventive methods and related devices involve geometric reshaping of the heart. In certain aspects of the inventive methods and related devices, substantially the entire chamber geometry is altered to return the heart to a more normal state of stress. Models of this geometric reshaping, which includes a reduction in radius of curvature of the chamber walls, can be found in U.S. Pat. No. 5,961,440, issued Oct. 5, 1999 and entitled "Heart Wall Tension Reduction Apparatus and Method," the complete disclosure of which is incorporated herein by reference. Prior to reshaping the chamber geometry, the heart walls experience high stress due to a combination of both the relatively large increased diameter of the chamber and the thinning of the chamber wall. Filling pressures and systolic pressures are typically high as well, further increasing wall stress. Geometric reshaping according to the present invention reduces the stress in the walls of the heart chamber to increase the heart's pumping efficiency, as well as to stop further dilatation of the heart.

Although many of the methods and devices are discussed below in connection with their use in the left ventricle of the heart, these methods and devices may be used in other chambers of the heart for similar purposes. One of ordinary skill in the art would understand that the use of the devices and methods described herein also could be employed in other chambers of the heart. The left ventricle has been selected for illustrative purposes because a large number of the disorders that the present invention treats occur in the left ventricle.

Reference will now be made in detail to the present preferred embodiments of the invention, examples of which are illustrated in the accompanying drawings. Wherever possible, the same reference numbers will be used throughout the drawings to refer to the same or like parts.

Figure 14:
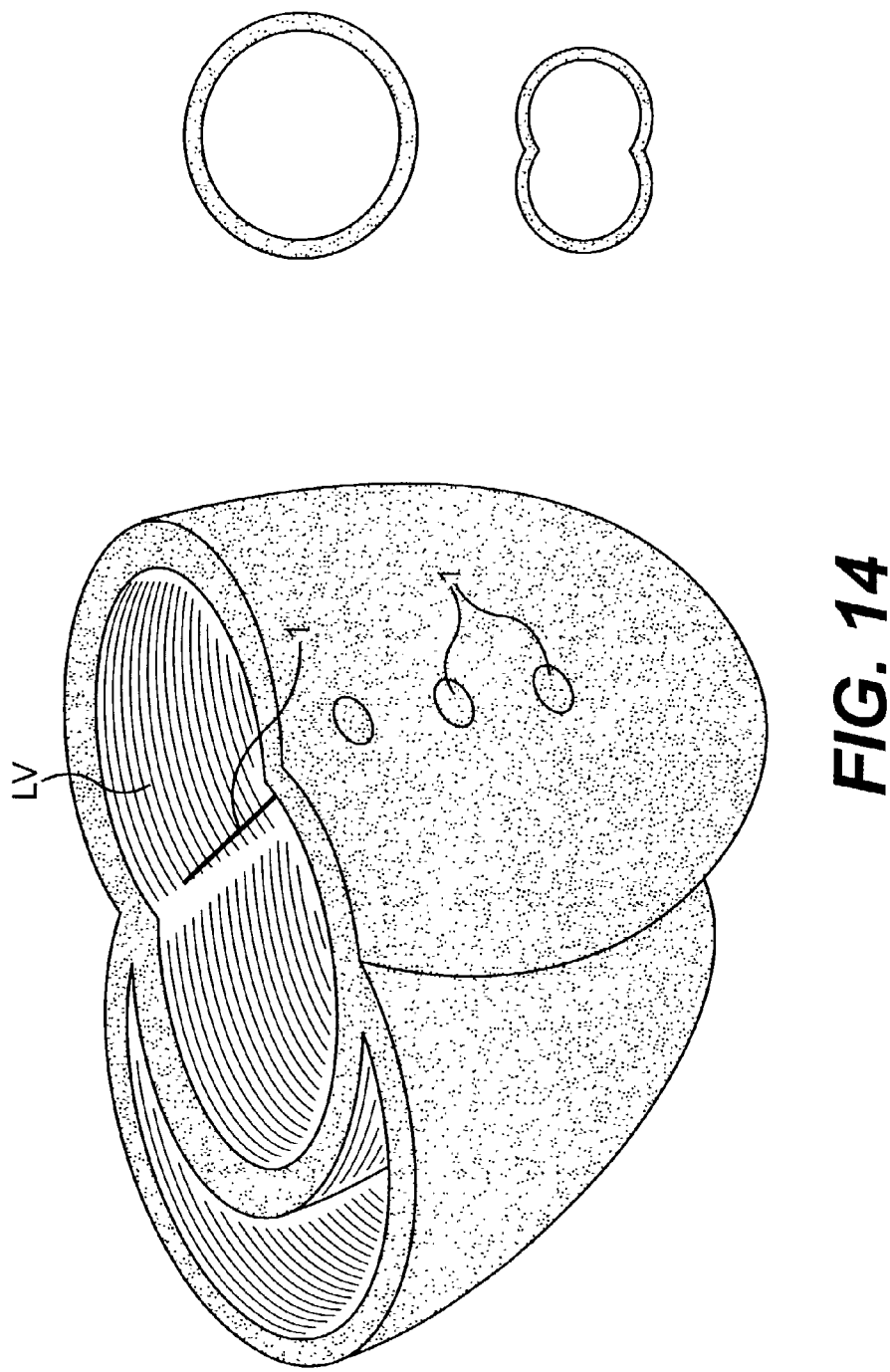
FIG. 14 is a cut-away perspective view of the heart showing a preferred placement of three splint assemblies for treatment of the heart according to the present invention and showing the cross-sectional shape of the left ventricle before and after placement of the splint assemblies with respect thereto.

FIG. 1 shows a splint assembly 1 that ultimately is placed in the heart and a leader assembly 10 connected to splint assembly 1 prior to placement of splint assembly 1 and aiding in the delivery of splint assembly 1 into the heart. Splint assembly 1 includes an elongate tension member 2 (shown by the thicker line), a fixed pad assembly 3, and an adjustable pad assembly 4. Fixed pad assembly 3 is disposed at one end of tension member 2 (which will be referred to as the proximal end of assembly 1), while adjustable pad assembly 4 is disposed to slidably engage tension member 2 and secure to tension member 2 opposite to the end attached to fixed pad assembly 3 (which will be referred to as the distal end of assembly 1). Preferably, splint assembly 1 is placed transverse a heart chamber to induce a shape change of the heart chamber, for example, the left ventricle, to reduce stress on the heart wall and thereby improve cardiac function. For example, as shown in FIG. 14, in a preferred embodiment of the present invention, three splint assemblies 1 are placed relative to the left ventricle LV in the manner illustrated to alter the shape of the ventricle from an essentially circular cross-section to an essentially bi-lobed cross-section. Although three splint assemblies are shown in FIG. 14, it is contemplated that any number of splint assemblies may be placed as desired, depending on the condition of the heart and the desired shape change results. Details on methods and tools used to determine the location for placement of the splint assembly 1 with respect to the heart chamber will be described later in this specification.

Splint leader assembly 10 includes a leader tube 5 (shown by the thinner line in FIG. 1 leading to tension member 2) and a stop band 7. Leader tube 5 facilitates the advancement of tension member 2 through the heart wall and across the heart chamber, as will be described. Once tension member 2 has been placed with respect to the heart and adjustable pad assembly 4 has been secured into place, leader assembly 10 and any excess tension member length can be severed and removed from tension member 2, for example, by thermal cutting or the like. Preferably, leader tube 5 is made of a high strength, substantially rigid, polymeric tubing, such as polyetheretherketone (PEEK), polyamide, polyimide, acetal, urethane, polyester, or other suitable like material. Leader tube 5 has an inner diameter of approximately 0.015 inches, an outer diameter of approximately 0.031 inches, and a length of approximately 24 inches.

Referring to FIG. 1, a distal end of leader tube 5 is hollow and heat-set into a coil shape. The coil shape provides leader tube 5 with a more compact configuration prior to implantation of splint assembly 1. This compact configuration is especially important as the splint assembly rests in a sterile environment prior to the implantation procedure. Moreover, the leader tube 5 will be less cumbersome for a surgeon to handle due to its compactness.

Secured around leader tube 5, preferably approximately 8 inches from its distal end, is a stop band 7. Stop band 7 engages with a measuring/tightening device which will be described in more detail later during a discussion of the implantation procedure of splint assembly 1. Preferably, stop band 7 is swaged about leader tube 5 and further secured, if necessary, through the use of an adhesive, such as, for example urethane or epoxy, or other suitable adhesive. To provide a smooth, tapered transition between stop band 7 and leader tube 5, a "backfill" or fillet 7' of adhesive is placed at the distal end of stop band 7. This fillet 7' permits a smooth engagement of stop band 7 to the measuring and tightening device. The measuring and tightening device and the engagement of stop band 7 with the device will be described later.

Referring to FIG. 2A, which shows an enlarged view of region A—A in FIG. 2, a portion of leader tube 5 contains a mandrel 6 within the lumen of leader tube 5. Mandrel 6 is secured to leader tube 5 by, for example, a suitable adhesive, such as, epoxy, or other suitable means such as a friction fit within tube 5. Mandrel 6 provides stiffness and support to leader tube 5. Additionally, mandrel 6 provides a base structure upon which stop band 7 can be swaged, thereby strengthening stop band 7. Preferably, mandrel 6 is made of stainless steel or other suitable material offering stiffness and support. Mandrel 6 extends within a proximal portion of leader tube 5 (closest to splint assembly 1) to a point within leader tube 5 slightly past stop band 7 before the coiled portion of leader tube 5. Mandrel 6 also extends from leader tube 5 and into a proximal end of tension member 2 to connect leader tube 5 with tension member 2.

Because the connection between leader tube 5 and tension member 2 undergoes relatively large tension stresses during tightening of the tension member, especially during implantation, which will be described later, the connection between the two should be strong. Thus, in a preferred embodiment, mandrel 6 includes a larger diameter portion 6' at its proximal end within tension member 2. This larger diameter portion is formed by centerless grinding of all but the proximal end of the wire forming mandrel 6. In a preferred embodiment, this wire is fabricated from a 0.020 inch diameter wire, with the ground portion having a diameter of 0.010 inch.

Mandrel 6 is fixed within a distal end of tension member 2, which includes a covering 11 surrounding an inner cable 11'. Mandrel 6 and a surrounding metallic tube 9 are covered with an adhesive 9' and inserted approximately 0.3 inches inside the distal end of tension member 2. An external metallic tube 12 is placed around a distal portion of covering 11 and cable 11' and is swaged down and secured thereto. An adhesive 12' is disposed between external metallic tube 12 and covering 11 to more firmly secure tension member 2 and tube 12.

Furthermore, adhesive 12" can be disposed at the distal end of metallic tube 12 to form a tapered connection between metallic tube 12 and leader tube 5. Once adhesive 12' is applied and tube 12 is swaged down, mandrel 6 and metallic tube 9, and tension member 2 are secured together. A smooth and secure mechanical connection thereby results between leader tube 5 and tension member 2.

Figure 4:
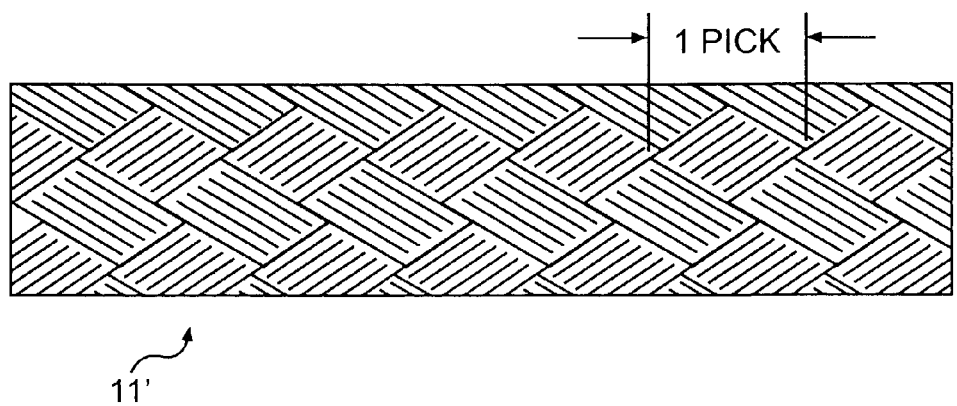
FIG. 4 is a magnified view of an embodiment of the cable forming the tension member according to the present invention.

Tension member 2, and particularly cable 11', serves as the primary load-bearing component of the splint assembly. Therefore, cable 11' preferably has a braided-cable construction, for example, a multifilar braided polymeric construction. In general, the filaments forming cable 11' should be high performance fibers. Preferably, filaments of ultra high molecular weight polyethylene, such as, for example, Spectra™ or Dyneema™, or some other suitable like material, such as polyester (e.g. Dacron™) or liquid crystal polymers (e.g. Vectran™), for example, will be used to form the braided cable. Filaments preferably are combined in yarn bundles of approximately 50 individual filaments, with each yarn bundle being approximately 180 denier. In a preferred arrangement, two bundles can be paired together (referred to as 2-ply) and then braided with approximately 16 total bundle pairs to form cable 11'. In this manner, the preferred braid includes approximately 20 to 50 picks per inch, and more preferably approximately 30 picks per inch, wherein one pick measured along the length of cable 11' is shown in FIG. 4. Thus, making the braid as described results in an average diameter of cable 11' of approximately 0.030 to 0.080 inches, and preferably 0.055 inches, having approximately 1600 individual filaments. In cross-section, the braided cable 11' appears somewhat oval. FIG. 4 shows a magnified view of a cable made according to the preferred embodiment described.

The preferred embodiment of cable 11' provides cable 11' with several significant properties. First, the ultra high molecular weight polyethylene provides cable 11' with high strength characteristics. Thus, cable 11' is able to withstand the constant tension that will be placed upon it during use within the heart. Additionally, this material has a high creep resistance, a high corrosion resistance, high fatigue resistance and is biostable. It is contemplated that other materials having similar properties also may be used to form cable 11' and are within the scope of this invention.

Forming cable 11' as a braided structure, and preferably in the manner described above, further provides cable 11' with high endurance to cyclic fatigue and resistance to shape change without interfering with heart structure. Implantation in the heart subjects cable 11', and therefore tension member 2, to a dynamic, and often cyclic, bending and stressing environment. A multifilar structure results in lower bending stresses than would otherwise occur in a solid structure. Moreover, a braided multifilar structure dissipates concentrated loads to adjacent filaments within relatively short distances as compared with a twisted multifilar structure. The braided structure also provides a simple, yet effective, way to anchor tension member 2 to pad assemblies 3 and 4, as will be explained in greater detail shortly.

Experiments have shown that a cable 11' of the preferred diameter range of 0.030 to 0.080 inches, and most preferably 0.055 inches, results in a high break strength and a high resistance to creep failure under expected stress conditions when placed in the heart. This resistance to creep strength allows cable 11' to maintain its shape throughout implantation and use of the device. Furthermore, a cable of the preferred diameter range permits pins to penetrate the cable to hold it in place in the fixed pad assembly. If the diameter were too small, the pins may pull on portions of cable 11', thus distorting the uniform shape of the cable. Additionally, it is important that cable 11' not have too large of a diameter. If the diameter is too large, blood flow in the chamber may be disrupted, increasing the risk of stasis or other flow disruptions, which can lead to thrombus formation and possible embolization. Moreover, an overly large diameter may result in damage to the tissue forming the heart wall at the implantation sites. Also, a larger diameter tension member increases difficulty of delivery and implantation in the heart.

Also under expected stress conditions when cable 11' is placed in the heart, the preferred range of picks per inch discussed above produces a braid that will resist fatigue and localized bending due to an increased hold strength. Experiments have shown that if the pick count is too low, for example below approximately 15 picks/inch, a low integrity, less stable braid having a tendency to unravel when connected to the pins, as will be described, will be produced. In addition, too low of a pick count results in less load sharing between yarn bundles and filaments, which, aside from contributing to a less stable braid structure, creates the potential for greater axial fatigue degradation. On the other hand, too high of a pick count, for example, above approximately 60 picks/inch, results in a braid that exhibits excessive wear due to contact stresses between the individual filaments, thereby presenting a risk of the filaments weakening and even fracturing. Moreover, such a high pick count creates a cable that is more susceptible to kinking.

As for the parameters of the yarn filament bundles themselves, pairing two bundles (i.e., two-ply) of 180 denier each has been shown to yield a high break strength, and also to assist in preventing creep under expected stress conditions when a cable 11' is placed in the heart. However, a finer yarn can be used if the number of bundles is increased, without departing from the desired strength and size of the overall braided cable.

Overall, the preferred combination of yarn density and material, together with the preferred pick count and cable diameter, results in an optimal tension member performance. That is, the tension member is capable of withstanding the cyclical stresses occurring within the heart chamber without breaking or weakening and a strong connection between the tension member and the pad assemblies can be achieved. Also, damage to internal vascular structure and the heart tissue, and obstruction of blood flow within the heart chamber can be avoided. Although the preferred parameters for the braid structure have been described above, it is contemplated that other combinations of material, yarn density, number of bundles, and pick count may be used, as long as the desired characteristics with respect to strength of the braid and interaction of the braid with the heart and blood are achieved.

Covering 11 surrounding cable 11' also provides tension member 2 with properties that facilitate implantation and use in the heart. Because tension member 2 will be in blood contact as it resides within a chamber of the heart, covering 11 preferably provides tension member 2 with resistance to thrombus generation. Furthermore, as a result of the relative motion that occurs between the heart and the portions of tension member 2 passing through the heart chamber wall, irritation of the heart wall may result. To alleviate such irritation, covering 11 preferably allows for tissue ingrowth to establish a relatively firm bond between the tension member and the heart wall, thus reducing relative motion between the two.

To achieve these advantages, covering 11 preferably is made of a porous expanded polytetrafluoroethylene (ePTFE) sleeve having an inner diameter of approximately 0.040 inches and a wall thickness of approximately 0.005 inches prior to placement around cable 11'. The inner diameter of covering 11 stretches to fit around cable 11', which preferably has a diameter of about 0.055 inches, resulting in a frictional fit between covering 11 and cable 11'. Preferably, covering 11, made of ePTFE, has an internodal distance of between 20 and 70 microns, and most preferably approximately 45 microns. This preferred internodal spacing achieves both secure tissue ingrowth of the adjacent heart wall by allowing cellular infiltration and creating a tissue surface on the outside of the tension member 2. The preferred internodal spacing also achieves a high resistance to thrombus. Furthermore, such a covering is biostable and tends not to degrade or corrode in the body. Although cable 11' primarily bears the loads placed on tension member 2, covering 11 also must be adapted to withstand the cyclic bending environment occurring in the heart. The porous nature of covering 11, particularly having the internodal spacings discussed above, enables bending without creating high stress regions that may otherwise result in fatigue cracking of the covering if a solid structure were used. Although expanded PTFE has been described as the preferred material With which to make covering 11, other suitable materials exhibiting similar characteristics also are within the scope of the invention.

Figure 3:
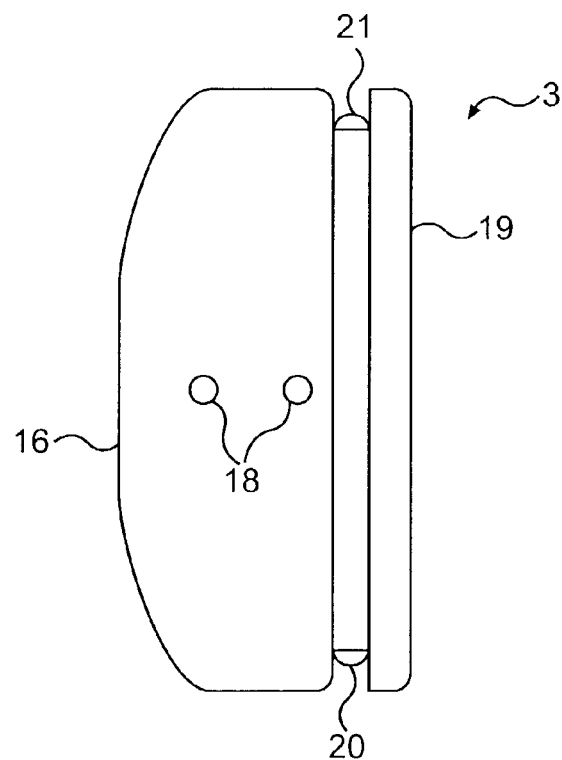
FIG. 3 is a perspective view of the fixed pad assembly of FIG. 2 looking into the pin channels of the assembly.

The remaining components of splint assembly 1 shown in FIG. 1 include fixed pad assembly 3 and adjustable pad assembly 4. These pad assemblies essentially function as anchors that engage with the heart wall, providing a surface adjacent the exterior of the heart wall to which the tension member connects and which does not penetrate the heart wall. FIGS. 2 and 3 show details of fixed pad assembly 3 and its connection to tension member 2.

As shown in FIGS. 2 and 3, fixed pad assembly 3 includes a pad base 15 made of a rigid thermoplastic such as polyetheretherketone (PEEK), or other suitable like material, such as, for example, polysulfone, polymethylpentene, or polyacetal (Celon). The selected material should be machinable and, if desired, moldable. Pad base 15 preferably has a generally disc-shaped configuration with a diameter of approximately 1 cm to 3 cm, preferably approximately 1.9 cm, and a thickness of approximately 0.3 cm to 1.5 cm, preferably 0.9 cm. A surface 16 adjacent the heart wall preferably is slightly convex with a radius of curvature of approximately 0.25 in. to 1.0 in, preferably approximately 0.5 in. Providing such a smooth, rounded surface 16 adjacent the heart wall tends to reduce localized compressive pressures that may otherwise be exerted on the heart wall. Such reduction in localized compressive pressure reduces the risk of necrosis of the heart tissue, which ultimately could lead to pad base 15 migrating through the thickness of the heart wall.

The preferred ranges for the diameter of pad base 15 discussed above results in optimal shape change and compressive forces on the heart chamber. Experiments have shown that if the pad base diameter is too large, i.e., above the high end of the preferred range discussed above, an optimal bi-lobed shape change to the heart chamber does not result. That is, the heart wall at the locations of excessively large pads tend to flatten out such that the radius of curvature at those locations is essentially zero. Overly large pad base diameters also make it difficult to place the pad assembly to avoid damaging vasculature of the heart. On the other hand, the experiments have shown that if the diameter is below the low end of the preferred range, the tension that is placed on the large tension member to draw the heart walls together will result in a compressive force on the heart that is too large, thus causing necrosis of the heart tissue. Such necrosis of the tissue likely will cause the pad to migrate into the heart wall of the ventricle. The diameter of pad base 15 should therefore be large enough to prevent such migration. The preferred pad base dimensions indicated above take these considerations into account, preventing migration and preventing undesirable shape changes of the heart wall.

A channel 17 extends through approximately the center of pad base 15 from an outer surface 19 to inner convex surface 16. Channel 17 has a diameter of approximately 0.062 inches through which tension member 2 passes. At inner surface 16, channel 17 has a slightly rounded, or tapered, opening 17' leading into channel 17. The tapered opening 17' has a radius of curvature of approximately 0.062 inches at the inlet into the pad and a diameter of approximately 0.064 inches. The opening tapers to the channel 17. This tapered opening, which has a diameter larger than tension member 2 permits tension member 2 to gently curve around inner surface 16 as relative bending occurs, as opposed to having a sharp bend that would otherwise result if the diameter were not enlarged in this region. This tapered opening decreases localized stresses in the region of tension member 2 near the opening to channel 17 that would occur during cyclical motion of the heart. Also, the diameter of channel 17 is slightly larger than the diameter of tension member 2 to permit room for the pins to penetrate the tension member to secure the tension member and pad together.

Two channels 18 extend in direction parallel to surfaces 16 and 19 across pad base 15. Channels 18 house fixation members, such as sharpened pins 14. Channels 18 preferably have a smaller diameter than the pin diameters to create a press fit during connection of fixed pad assembly 3 to tension member 2. For example, channels 18 preferably have a diameter of approximately 0.028 inches, as opposed to pin diameters of approximately 0.030 inches.

A preferred embodiment of pad base 15 includes a circumferential groove 20 adjacent to outer surface 19, as shown in FIG. 2. Circumferential groove 20 accomodates windings of suture 21 to be secured to pad base 15. In this way, a pad covering 13 (shown in FIG. 2) can be placed over inner surface 16 and sides of pad base 15 and secured with respect thereto via suture windings 21. Any excess pad covering extending past suture windings 21 can be trimmed off. Pad covering 13 preferably is made of a velour woven polyester material, such as Dacron™, or other suitable like material, such as, for example, expanded polytetrafluoroethylene (ePTFE). The pad covering facilitates ingrowth of the heart wall tissue to secure pad base and thereby prevent long-term, motion-induced irritation of the outside of the heart wall. A hole disposed in approximately the center of the pad covering enables the passage of tension member 2. A similar pad covering connects in the same manner to a circumferential groove and sutures located on adjustable pad assembly 4, as will be described later.

To secure fixed pad assembly 3 to tension member 2, fixation members, such as pins 14, extend through channels 18 and penetrate through covering 11 and cable 11'. Pins 14 can be sharpened on their ends to more easily pierce through covering 11 and cable 11'. As shown in FIG. 2, tension member 2 folds over within pad base 15 in a U-shaped configuration. In this way, pins 14 each penetrate at an additional site along tension member 2 to provide a stronger connection between tension member 2 and fixed pad assembly 3. The penetration of each pin 14 through two points of braided cable 11 provides a reliable connection. This is due to the fact that the braided structure tends to transfer the contact load produced by pins 14 against the filament bundles and to all of the filaments forming braided cable 11', essentially resulting in a load distribution between the pins and filaments.

A reliable connection could be produced using only a single pin penetrating through the tension member at a single location. However, providing more than one pin and folding tension member 2 into the U-shaped configuration so that each pin intersects tension member 2 at more than one location offers additional strength to the connection. In essence, this configuration serves as a safety back-up should the connection at a single pin/cable interface become unsecure. Unless a failure at one of the pin sites occurs, however, it is expected that the intersection between the distal-most pin and the location where that pin first intersects tension member 2, as tension member 2 enters pad base 15, will carry substantially all of the load transferred by tension member 2. This intersection site is labeled as 14a in FIG. 2.

It is preferable for pins 14 to penetrate tension member 2 at approximately the center of the cable to provide the most secure connection. Thus, approximately half of the filament bundles comprising the entire cable will be on one side of a pin and half on the other side. Such a placement of pins 14 assists in inhibiting distortion of the braided structure resulting from a non-equal distribution of the load on the various filaments. Additionally, to inhibit distortion of tension cable 11', preferably a relatively dense braid is formed (i.e., in terms of both pick count and number of bundles) so pins 14 can penetrate and be secured without risk of pulling out or unraveling the braid.

Furthermore, some length of cable 11' should extend on either side of pins 14 so that pins 14 are not easily pulled through the braid along the length of the braid. In this manner, preferably, at least one of pins 14 penetrates cable 11' at a location that leaves a length of cable of approximately 1 to 2 centimeters. For example, the folded over configuration of tension member 2 within fixed pad assembly 3 serves to prevent both pins 14 from becoming disengaged with tension member 2 as a result of cable 11' unraveling at its end. To further prevent unraveling of cable 11', tension member 2 can be thermally treated or otherwise fused together at its end.

In a preferred embodiment, fixed pad assembly 3 includes two pins 14 of approximately 0.025 to 0.035 inches in diameter and length slightly less than the pad base diameter, as shown in FIG. 2. Pins 14 can be formed of a relatively hard, corrosion-resistant material, such as, for example, a cobalt-nickel-chromium-molybdenum alloy, such as MP 35N, other cobalt-chrome alloys, stainless steel, or other suitable materials having similar characteristics. At least one end of each pin preferably is sharpened to facilitate penetration of tension cable 11' and covering 11.

With reference to FIGS. 1 and 5–7, adjustable pad assembly 4 and its connection to tension member 2 will now be described. The general outer configuration of adjustable pad assembly 4 is similar to that of fixed pad assembly 3. That is, adjustable pad assembly 4 includes a convex inner surface 47 that engages with an exterior of the heart wall when splint assembly 1 is implanted in the heart. Also, near an outer surface 48 of adjustable pad assembly 4 is a circumferential groove 80 with suture windings 81. Although not shown in the Figures, it is contemplated that a pad covering of the type described with reference to fixed pad assembly 3 will be provided and secured via suture windings 81 to facilitate tissue ingrowth between adjustable pad assembly 4 and the heart wall.

Figure 5:
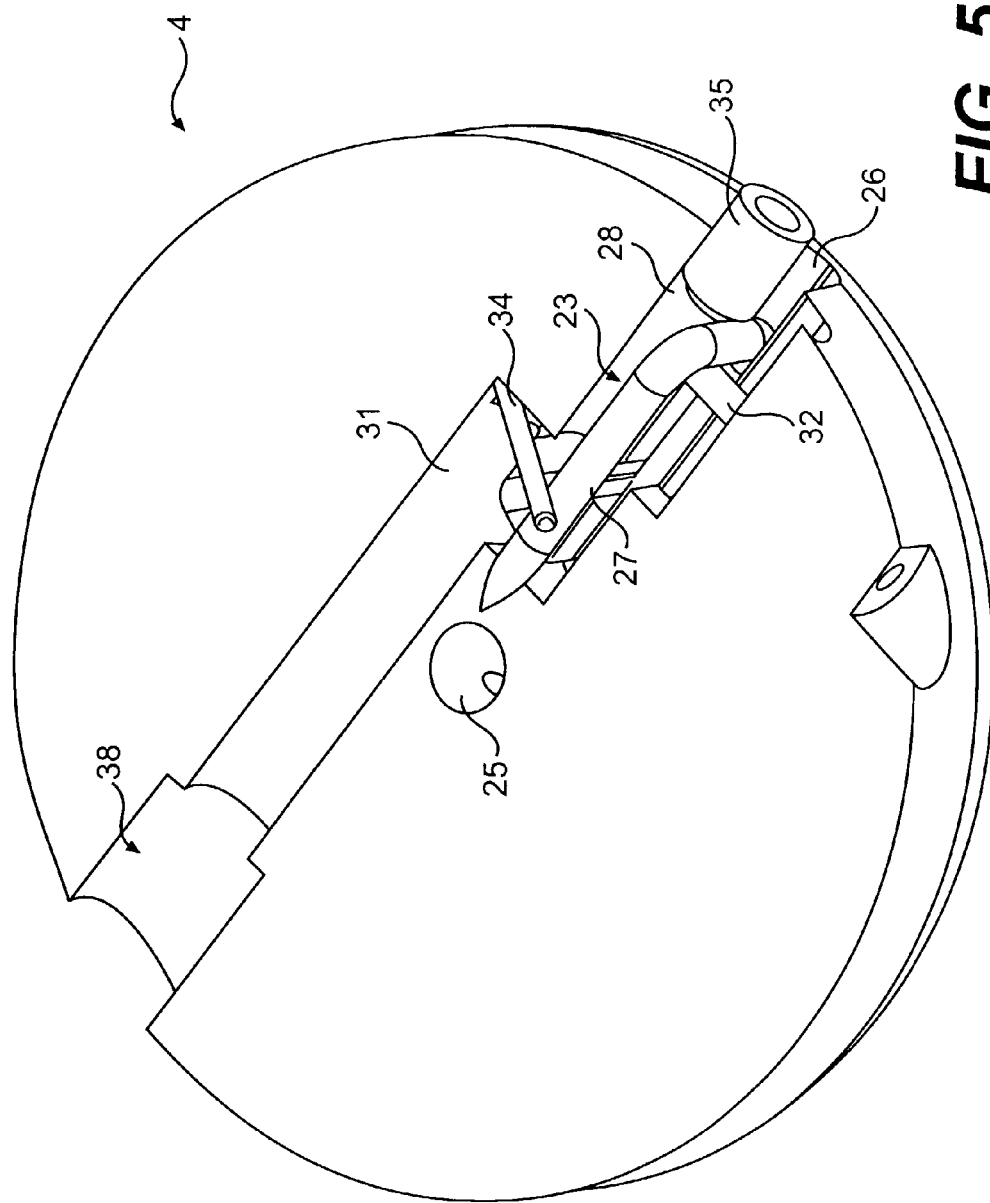
FIG. 5 is a lateral cross-sectional view of an embodiment of an adjustable pad assembly according to the present invention.
Figure 6:
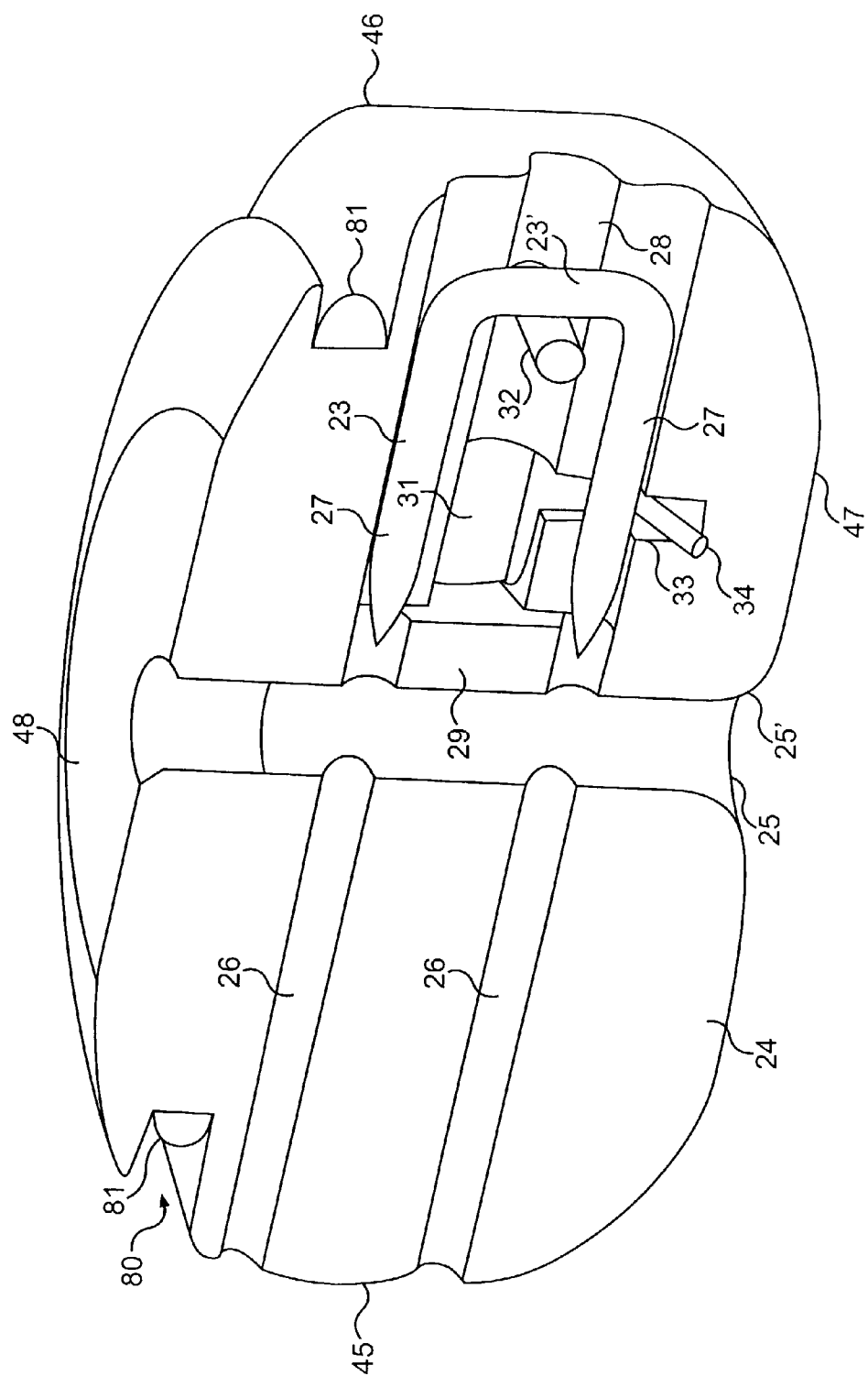
FIG. 6 is a vertical cross-sectional view of the adjustable pad assembly of FIG. 5 in a pre-deployment configuration according to the present invention.
Figure 7:
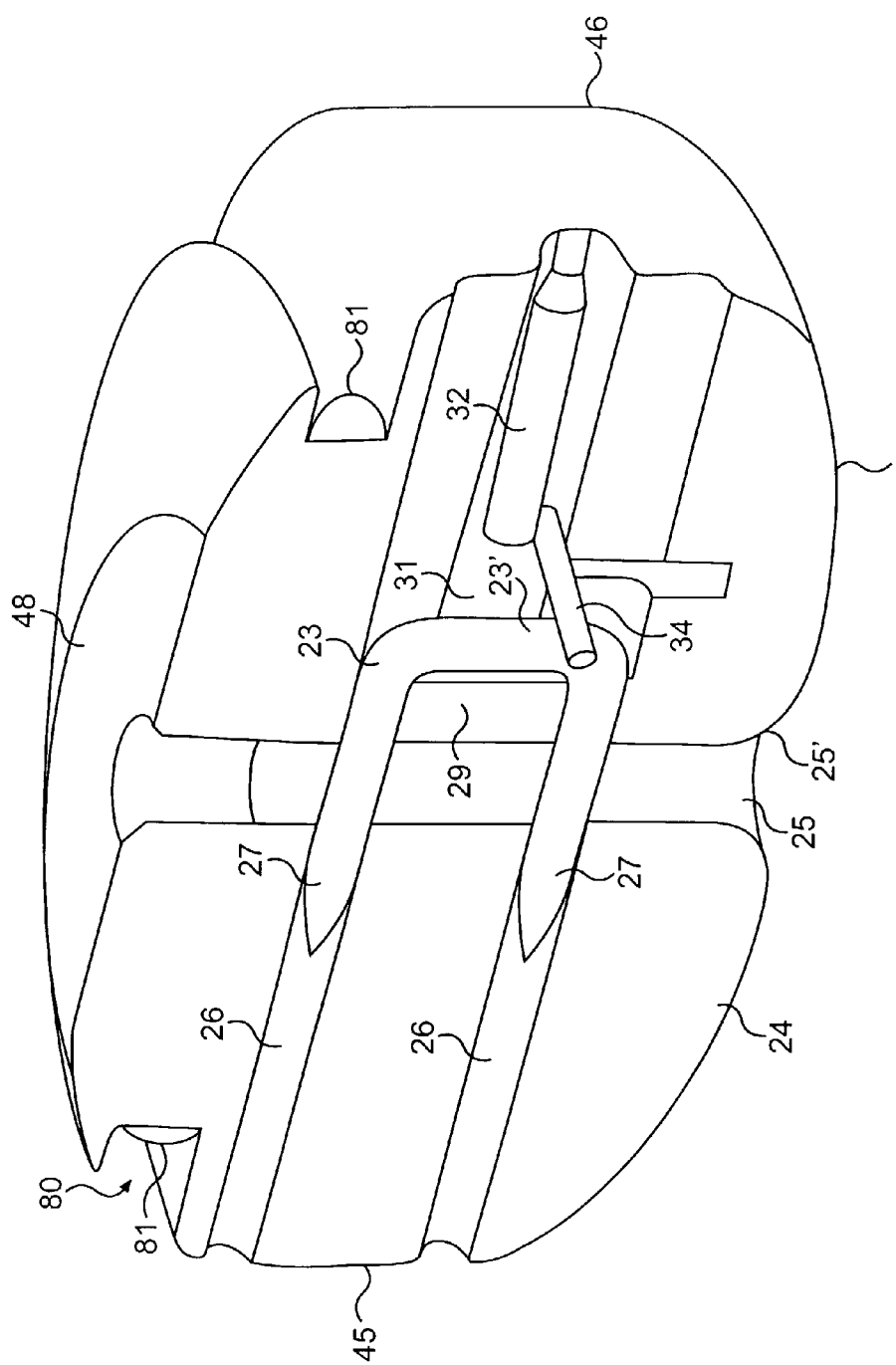
FIG. 7 is a vertical cross-sectional view of the adjustable pad assembly of FIG. 5 in a post-deployment configuration according to the present invention.

FIGS. 5–7 depict the inner components of adjustable pad base 24. As shown, pad base 24 includes a plurality of channels. A channel 25 through which tension member 2 passes extends through pad base 24 in a manner similar to channel 17 passing through pad base 15 of fixed pad assembly 3. FIGS. 5 and 6 more clearly show the tapered opening 25' of this channel 25 (similar to channel 17), which permits tension member 2 to gently curve at the surface of adjustable pad assembly 4. However, unlike channel 17, channel 25 in adjustable pad assembly 4 includes a further reduction in diameter, preferably approximately 0.059 inches, near an outer surface 48 of pad base 15. This reduction in diameter helps to assure that the braid of cable 11' is centered in channel 25 prior to fixation of tension member 2 to adjustable pad assembly 4. It is important for cable 11' to be centered within channel 25 to ensure that a fixation or securement member, for example in the form of a staple 23, used to secure tension member 2 to adjustable pad assembly 4, penetrates cable 11' in its center. In this manner, the yarn bundles of cable 11' evenly divide on either side of staple 23 to evenly distribute the load to tension member 2. Channel 17 in fixed pad base 3 does not require such a reduced diameter region since the securement of tension member 2 to fixed bad assembly 3 occurs under controlled factory conditions prior to implantation of splint assembly 1 in the heart.

A pair of staple leg channels 26 extend through pad base 24 substantially perpendicular to channel 25 and parallel to inner surface 47 and outer surface 48 of pad base 24. The pair of channels 26 merges into a single staple leg channel disposed on one side of channel 25. Channels 26 receive legs 27 of a staple 23 and are sized to enable staple 23 to slide along the channels from a retracted position (shown in FIG. 6) to an advanced position (shown in FIG. 7) upon actuation of a deployment tool 22, as will be described.

A channel 28 extends between and parallel to staple leg channels 26. Channel 28 is formed within one side of pad base 24 (on the side of a base 23' of staple 23 opposite to the side from which legs 27 extend) and extends for approximately two-thirds of the distance measured from the side of pad base 24 to the center of pad base 24. A deployment tool channel 31 begins at the end of channel 28 and extends through the remaining diameter of pad base 24. Deployment tool channel is radially offset from channel 28 and extends through pad base 24 so as to avoid intersection with channel 25.

A pre-deployment safety pin 32 is located approximately in the center of the portion of channel 28. Pre-deployment safety pin 32 extends essentially perpendicularly to channel 28 and engages with base 23' of staple 23 between staple legs 27 prior to actuation of staple 23. This engagement tends to hold staple 23 in place to prevent premature advancement.

A side channel 33 also is formed in pad base 24. Side channel 33 extends perpendicularly to staple leg channels 26. Side channel 33 begins on either surface 47 (which engages the heart wall) or surface 48 (which faces away from the heart wall) and extends to approximately the end of channel 28, near the beginning of deployment tool channel 31. A post-deployment safety pin 34 is disposed in side channel 33. Post-deployment safety pin 34 has a deflected configuration as it resides in side channel 33, pressing on the side of one of staple legs 27.

After tension member 2 has been extended transverse a heart chamber, for example, the left ventricle, such that the free end of tension member 2 extends through the heart wall at a location opposite to fixed pad assembly 3, leader tube 5 and tension member 2 are fed through channel 25 of adjustable pad assembly 4. Next, a measuring/tightening device, which will be described in more detail shortly, is used to determine and adjust the proper tension member length between fixed pad assembly 3 and adjustable pad assembly 4. This length is the length that is desired for the final implantation of splint assembly 1 in the heart. The determination of this length and the measuring and tightening procedure have been described in prior U.S. application Ser. No. 09/123,977, filed Jul. 29, 1998, and entitled "Transventricular Implant Tools and Devices," the complete disclosure of which is incorporated by reference herein. In general, the final length of the tension member when placed in the heart corresponds to a predetermined desired percentage reduction of the heart chamber diameter and the actual measured heart chamber diameter, which may differ from patient to patient.

Figure 8:
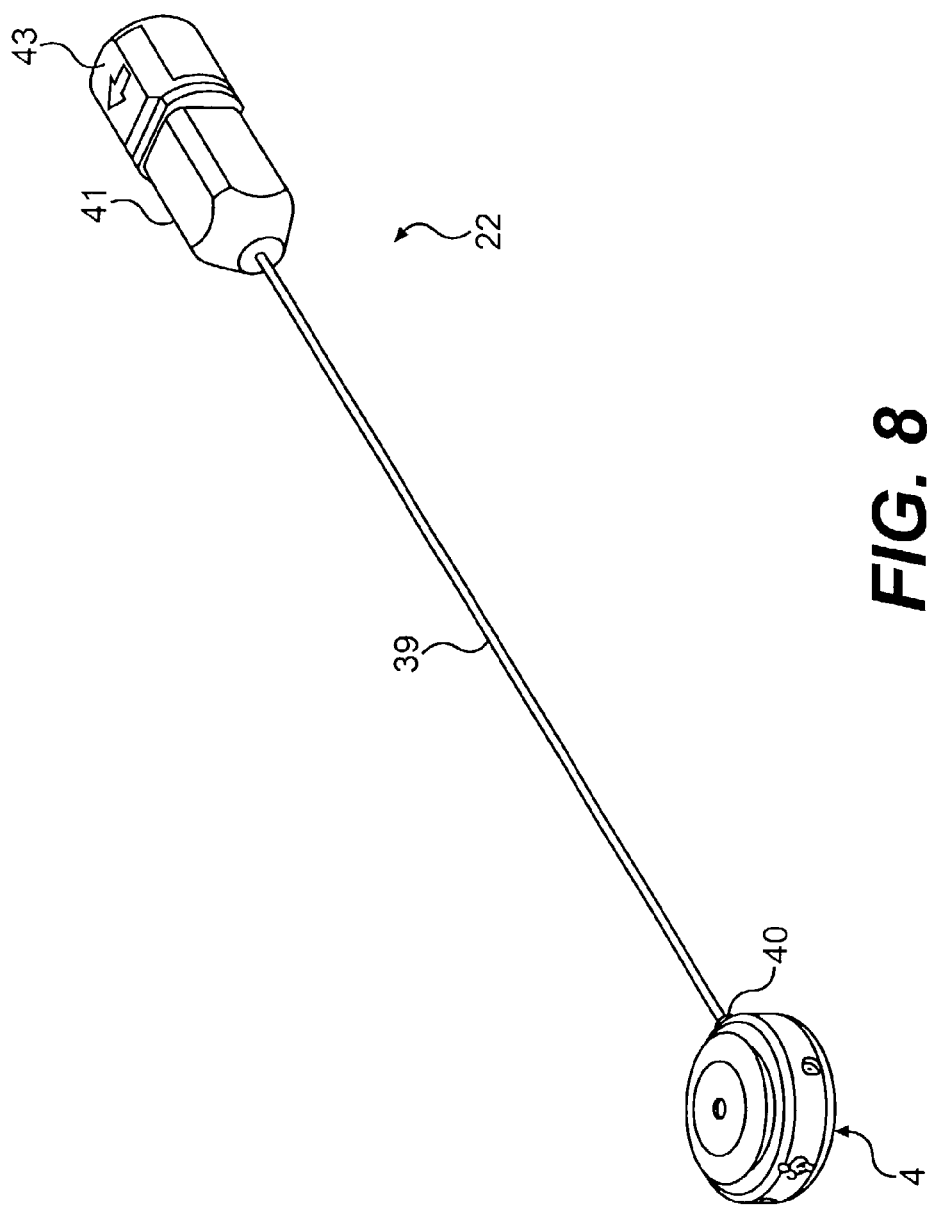
FIG. 8 is a perspective view of an embodiment of a deployment tool engaged with an adjustable pad assembly according to the present invention.
Figure 9:
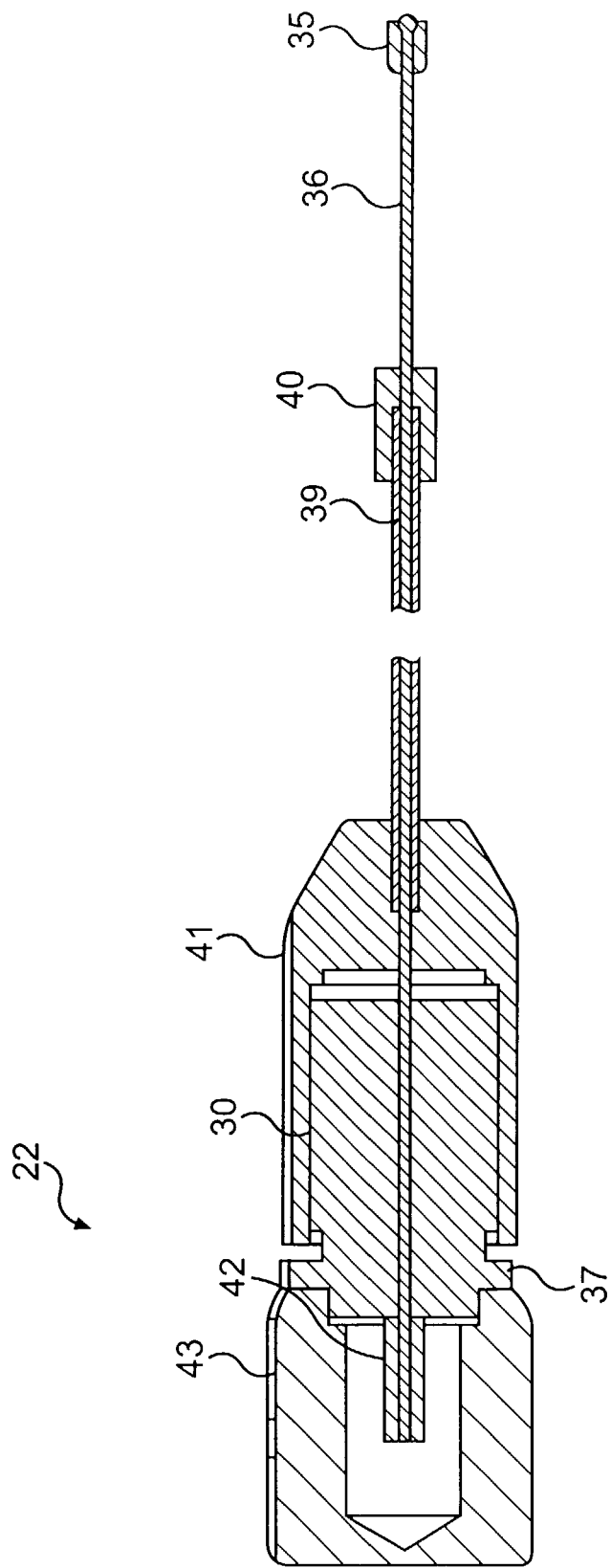
FIG. 9 is a cross-sectional view of an embodiment of the deployment tool of FIG. 8, showing the inner components thereof.

Once the desired implant length of tension member 2 has been determined, adjustable pad assembly 4 is placed in the proper position on tension member 2, with surface 47 engaging the outer surface of the heart wall. A deployment tool 22, shown in FIGS. 8 and 9 is used to secure adjustable pad assembly 4 into place on tension member 2. As mentioned earlier, a deployment tool 22 is pre-engaged with adjustable pad assembly 4. That is, deployment tool 22 includes an engagement collar 35 disposed in channel 28, as shown in FIG. 5, and an actuator wire 36 (not shown in FIG. 5) connected to engagement collar 35 at one end and to an actuator knob 37 at the other end. Thus, in the pre-deployment condition of staple 23, engagement collar 35 rests against staple base 23' and actuator wire extends from engagement collar 35 and through the entire diameter of pad base 24 exiting at a side 45 of pad base 24. At surface 45 of pad base 24, deployment tool channel 31 ends in a countersink region 38. At this location, actuator wire 36 runs through the center of, but is not affixed to, an outer coil 39. A collar 40 surrounds both outer coil 39 and actuator wire 36. Collar 40 rests within countersink region 38, essentially providing an abutment surface within pad base 24 that creates a counter-resistant force enabling actuator wire 36 to be pulled through pad base 24.

Referring to FIG. 9, actuator wire 36 and outer coil 39 connect to a threaded base portion 41 of deployment tool 22. Outer coil 39 terminates within threaded base portion 41. Actuator wire 36 continues through threaded base portion 41 and into an actuator 37. Actuator 37 also includes threads that engage with the threads of threaded base portion 41 at an interface 30. Actuator wire 36 fixedly attaches by a crimp fit 42 to a proximal end of actuator 37. An actuator knob 43 preferably is fixedly mounted to the distal end of actuator 37 to provide an ergonomic surface for a user to actuate deployment tool 22.

To deploy staple 23, actuator knob 43 is turned. This rotates actuator 37 with respect to threaded base portion 41, essentially unscrewing actuator 37 from threaded base portion 41. As actuator 37 turns, actuator wire 36 is pulled through outer coil 39, exerting a force on engagement collar 35. Continued rotation of actuator 37 further pulls on actuator wire 36 and engagement collar 35. Engagement collar 35 thus moves staple 23 within adjustable pad assembly 4 to move staple legs 27 along channels 26. Staple legs 27 eventually are pulled across channel 25, piercing through tension member 2 in approximately the center thereof.

To avoid, damage to staple 23, actuator wire 36 preferably rotates with respect to engagement collar 35 as actuator 37 turns without exerting any rotational forces upon engagement collar 35. In this manner, engagement collar 35 simply pushes against staple 23, but does not translate with respect to the staple surface. Thus, abrasive forces acting on staple 23 are avoided, which otherwise may cause scratches and lead to corrosion of the staple. In addition, excessive torque on actuator wire 36 by engagement collar 35 will be prevented.

As staple 23 moves within pad base 24, the base portion 23' of staple 23 bends pre-deployment safety pin 32 into the position illustrated in FIG. 7. Movement of staple 23 within pad base 24 continues until engagement collar 35 enters deployment tool channel 31. At this point, the inner surface of base 23' of staple 23 is disposed near or at abutment wall 29 of pad base 24. Once staple 23 advances to this position, base 23' has traversed past side channel 33. Thus, post-deployment safety pin 34 moves through side channel 33 and into deployment tool channel 31, as shown in FIG. 7. Post-deployment safety pin 34 moves to a perpendicular position, to serve as a mechanism for preventing staple 23 from moving back into staple leg channels 27. Abutment wall 29 prevents staple 23 from moving in the other direction through pad base 24. Preferably, after deflection, pre-deployment safety pin 32 does not lie entirely flush within channel 28 but rather deflects back up so that it extends slightly outside of channel 28. Thus, pre-deployment safety pin 32 serves as a safety backup to maintain the advanced position of staple 23 if post-deployment safety pin 34 should for some reason fail to do so.

Preferably, both pre-deployment and post-deployment safety pins are press-fit within pad base 24. The pre-deployment safety pin preferably has a diameter of approximately 0.025 inches and the post-deployment safety pin preferably has a diameter of approximately 0.016 inches. The pre-deployment pin preferably is made of annealed MP35N and the post-deployment pin preferably is made of spring-tempered MP35N. The annealing of pre-deployment pin 32 facilitates the formation of the permanent bend upon deflection resulting from advancing staple 23. The spring-tempering of post-deployment pin 34 enables the pin to recover to a relatively straight condition once the staple is fully deployed. It is contemplated that other means for moving pre- and post-deployment pins into their respective positions prior to and after deployment of staple 23, as well as other diameters and materials of such pins, are within the scope of this invention. For example, the pins could be spring-activated with a bias in a particular direction such that the pins would move into their appropriate positions during deployment of staple 23.

Although pre- and post-deployment safety pins 32, 34 serve as a back-up mechanism to prevent staple 23 from disengaging with tension member 2 and retracting back into its initial position within pad base 24, it should be noted that tension member 2 itself serves as the primary mechanism for preventing retraction of staple 23. That is, the force exerted by tension member 2 onto staple 23 as a result of tightening tension member 2 in place with respect to the heart chamber tends to prevent staple 23 from moving. Due to this relatively large force exerted between tension member 2 and staple 23, it is preferred to leave a length of tension member 2 of approximately 1 cm to 2 cm extending beyond the distal end of the distal most staple leg 27 to prevent staple 23 from pulling through the length of tension member 2. Leaving this length of tension member 2 is even more desirable in the connection of tension member 2 to adjustable pad assembly 4 than it is for fixed pad assembly 3 since tension member 2 is not folded over in the former. Moreover, as will be explained, it is preferred to melt or otherwise fuse the end of tension member 2 to prevent unraveling of cable 11'.

Once staple 23 has been deployed through tension member 2 and can no longer move within pad base 24, engagement collar 35 drops into deployment tool channel 31. By continuing to pull on actuator wire 36, engagement collar 35 can be pulled through deployment tool channel 31 and the entire deployment tool (including actuator wire 36 and engagement collar 35) can be removed from adjustable pad assembly 4.

After removing deployment tool 22, leader assembly 10 can be separated from tension member 2 using a conventional cauterizing pen, or other suitable like instrument. The end of tension member 2 left protruding from adjustable pad assembly 4 is also heated, or melted, and essentially fused together as a result of using the cauterizing pen to separate leader assembly 10. By fusing the end of tension member 2, the filaments of cable 11' and covering 11 are joined to prevent potential unraveling of the tension member braid. Other suitable mechanisms for severing the leader from the tension member and for fusing the tension member end also are within the scope of the invention. For example, although it is preferred to use the single step to both sever the leader assembly and fuse the tension member, it is also contemplated that the severing and fusing steps can be performed as separate steps.

Figure 10:
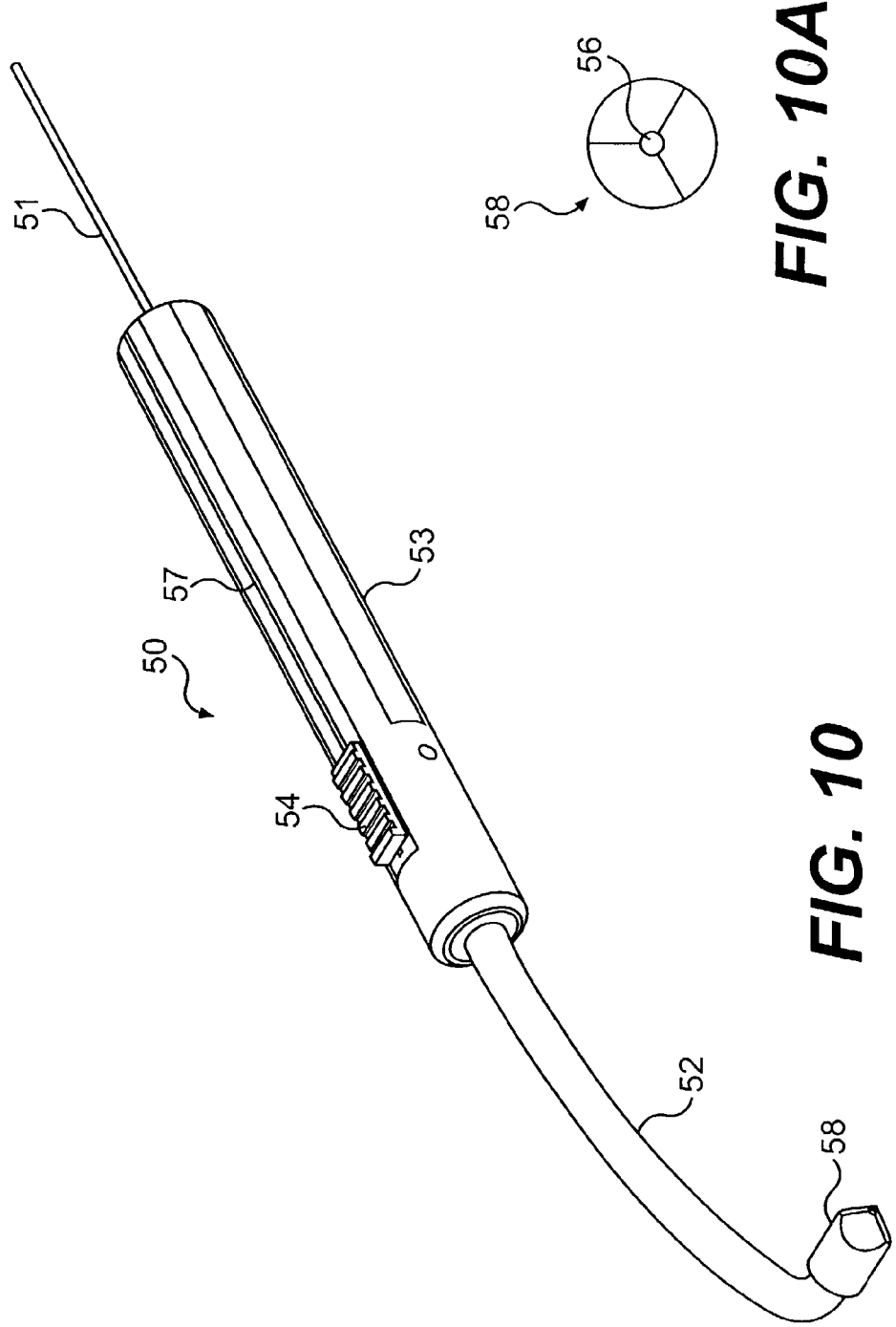
FIG. 10 is a perspective view of an embodiment of an probe/marking device according to the present invention.
Figure 11:
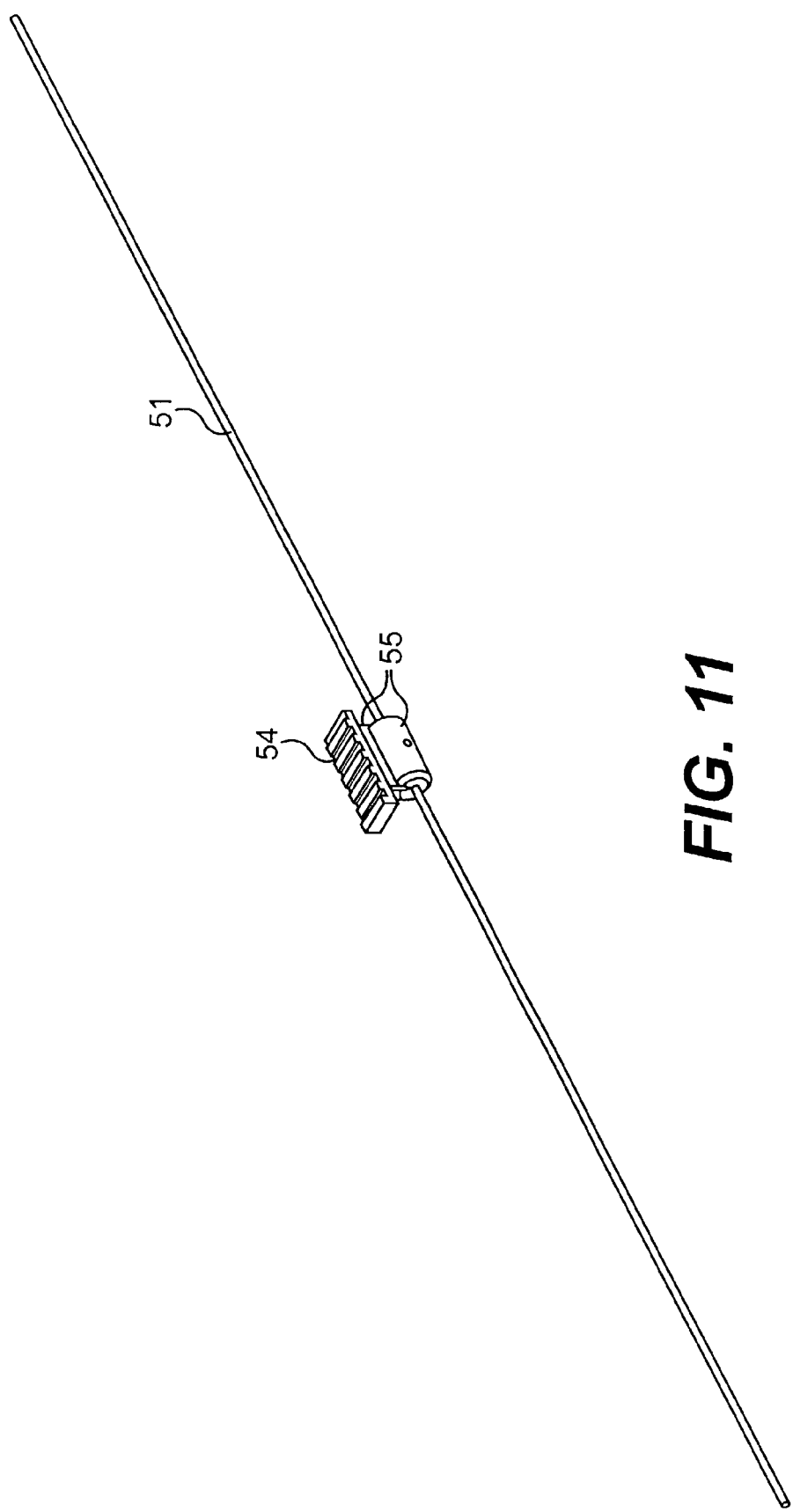
FIG. 11 is a perspective view of an embodiment of a tube used for housing a marker of the type shown in FIG. 12 prior to delivery according to the present invention.
Figure 12:
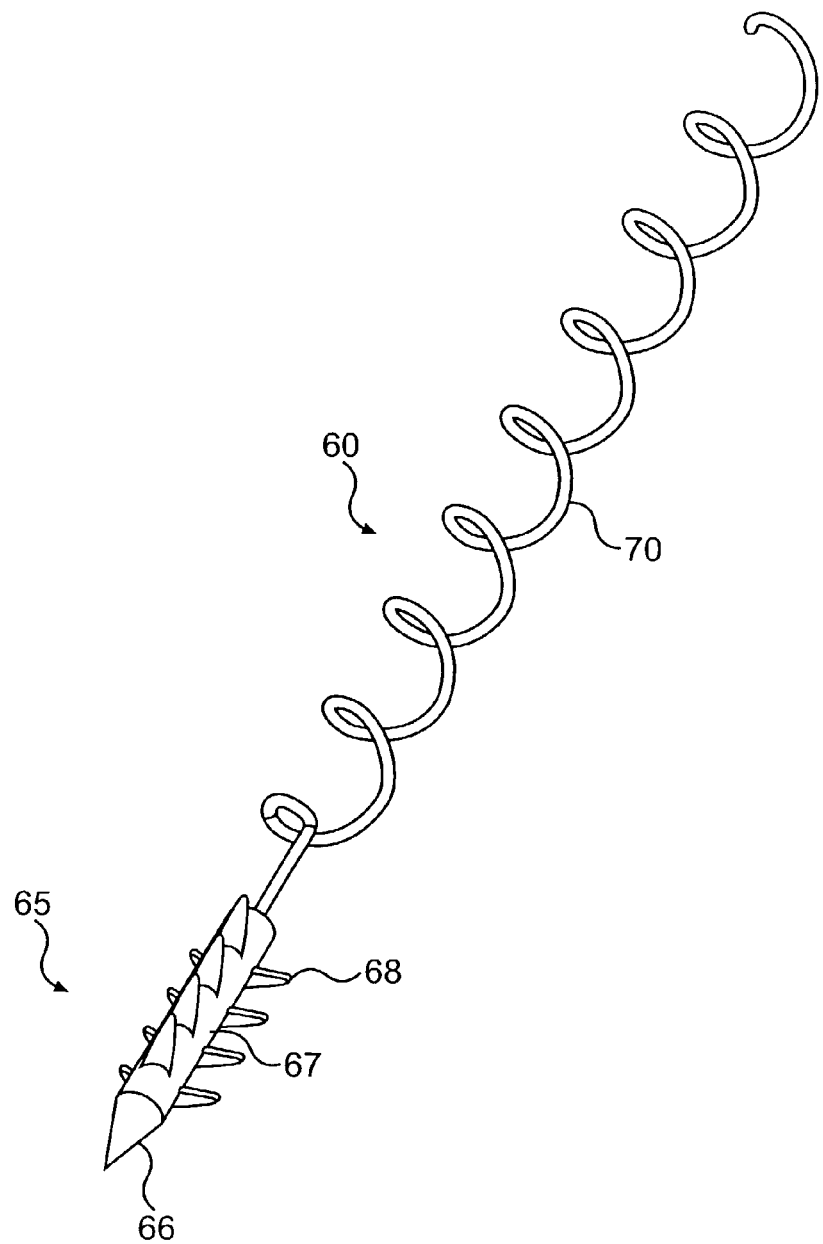
FIG. 12 is a perspective view of an embodiment of a marker according to the present invention.

Another aspect of the invention, described herein with reference to FIGS. 10–12, includes various location and identification tools for assisting in the optimal placement of splint assembly 1 with respect to a heart chamber to avoid damage to both internal cardiac structures, such as the papillary muscles, and external structures, such as blood vessels. Moreover, the tools assist in the placement of splint assemblies to effectively bisect the ventricle to result in optimal radius reduction and stress reduction.

Figure 13:
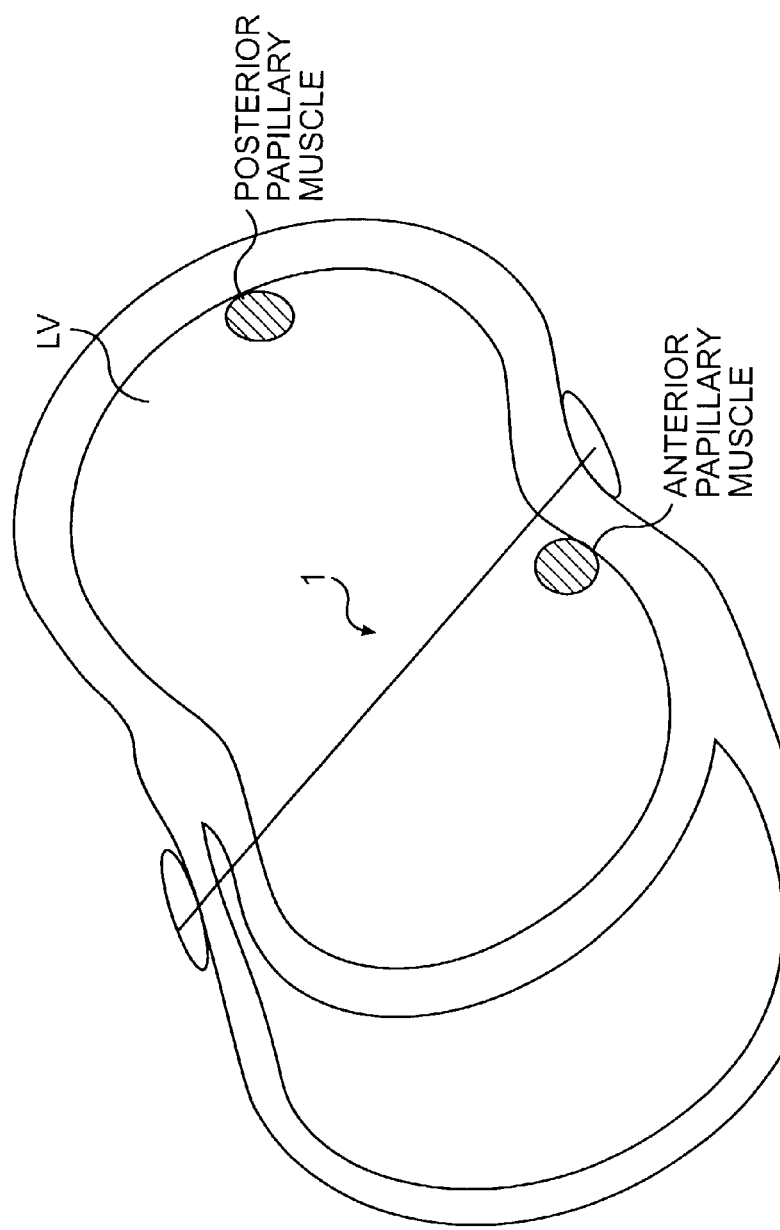
FIG. 13 is a cross-sectional view of the heart showing a preferred placement of one of the splint assemblies according to an embodiment of the present invention.

Although a number of possible orientations for splint placement are possible, in the surgical procedure of the present invention, preferably the splint assembly will be placed across the left ventricle in a plane essentially longitudinally bisecting the ventricle. The splint assembly should extend from a location proximate to the anterior papillary muscle on the ventricle free wall to a location proximate to the posterior ventricular septum. The preferred location for the splint assembly near the anterior papillary muscle is just lateral to that muscle, while the preferred location near the septum is on the posterior free wall of the right ventricle. FIG. 13 shows this preferred placement of a splint assembly.

In a preferred embodiment of the invention, as shown in FIG. 14, three individual splint assemblies 1 are implanted. The upper-most (basal) splint assembly is placed according to the description above. The remaining two splint assemblies will be positioned in an equidistant relationship between the basal splint assembly and the apex of the left ventricle. In this manner, the three splint assemblies essentially bisect the ventricle, producing optimal radius and stress reduction without excessive ventricular volume reduction. The positioning of the splint assemblies in this way also avoids interference with the mitral valve structure, including the chordae tendonae. Additionally, the positions described effectively avoid significant coronary arteries or veins.

Various types of surgical techniques can be employed to implant the splint assemblies of the present invention, including minimally invasive techniques through access ports, or endovascular techniques not requiring opening of the chest wall. These splint assemblies also could be implanted as an adjunct to other surgical procedures, such as, for example, CABG or mitral valve replacement. However, a preferred method of implanting the splint assemblies includes through an open chest sternotomy without cardiopulmonary bypass. The description of the identification and location tools and methods for implanting the splint assemblies that follows thus relates to such an open sternotomy procedure.

Visualization of the internal structures of the heart, including both the papillary muscles and the septum, typically occurs through the use of external imaging methods, since the internal structures can generally not be discerned from outside the heart chamber. A preferred external imaging method includes the use of ultrasound probes. Ultrasound probes can either be used direcly in contact with the outside of the heart or can be positioned in the patient's esophagus (transesophageal)

A probe/marking device 50, shown in FIG. 10, operates to both locate positions on the heart wall for splint placement and simultaneously deliver a marker into the heart wall to mark each location. Marker 60, shown in FIG. 12, is initially preloaded within a tube 51, shown in FIG. 11. Tube 51 houses the entire structure of marker 60 with the exception of a penetrating tip 65, which extends from a distal end of tube 51. Marker 60 thus can easily be removed from tube 51. Mounted on an exterior surface of tube 51 is an advancer button 54, the function of which will become apparent shortly.

Probe/marking device 50 includes a hollow handle portion 53, a shaft 52, and a probe tip 58. Handle 53 defines a slot 57 which opens at a proximal end and is configured to receive advancer button 54, as will be described shortly. Shaft 52 preferably is relatively rigid and may be curved as well, as shown in FIG. 10, to facilitate access to the exterior heart wall. Probe tip 58 preferably has an essentially conical shape with three flat angular faces. As shown in FIG. 10A, the three angular faces meet at the distal most portion of tip 58 to define an opening 56 through which marker 60 is configured to pass upon delivery. Probe tip 58 should be made of a material having a density that is sufficiently different than the myocardium in order to enhance echovisualization. A preferred material exhibiting this characteristic is a metal, such as stainless steel, for example, with a polyester covering such as Dacron™, or other suitable like material, that provides a gripping surface with respect to the heart tissue, to help stabilize the position of tip 58 with respect to the heart wall during indentation. The diameter of the proximal portion of tip 58 that connects to shaft 52 is approximately 0.375 in. This configuration aids in creating a distinct, localized deflection upon contact and indentation of the heart wall. Furthermore, the flat angular faces enhance the visualization of probe tip 58 using ultrasound since the reflections off of the edges of the faces produce more discrete lines on the echo-image and the flat faces tend to reflect the ultrasound signals to a greater extent than a curved face.

Prior to use, a physician inserts the distal end of a tube 51 preloaded with marker 60 into the proximal end of handle 53 of probe/marking device 50. As tube 51 is inserted, advancer button 54 slides into slot 57. Tube 51 is inserted into probe/marking device 50 until a base 55 of advancer button 54, which connects advancer button 54 to tube 51, engages with a detent mechanism (not shown) formed in handle 53. In this position, marker tip 66 is disposed at a location just proximal to the distal end of probe tip 58. Also, a portion of the proximal end of tube 51 extends from the proximal end of handle 53 of probe/marking device 50.

Probe tip 58 is then iteratively pressed against the outside of the heart wall to create localized indentations. Using ultrasound or other like imaging method, the physician can concurrently visualize these localized indentations, as well as tip 58, to determine the position of the indentations relative to internal heart structures. In addition, the flat faces and preferred material of probe tip 58 tend to create a shadow that can be seen in the ultrasound picture, thus improving visualization.

Upon finding a desired splint placement location, advancer button 54 is moved forward until it abuts the end of slot 57 defined by handle 53. Moving advancer button 54 forward within slot 57 in turn moves tube 51 forward so as to move marker tip 66 through opening 56 of probe tip 58. Marker tip 65 thus moves past probe tip 58 and into the heart wall.

FIG. 12 shows details of a preferred marker 60 to be used with inventive probe/marking device 50. Marker 60 includes a penetrating tip 65 and a suture line 70. Penetrating tip 65 includes a sharpened, conical-shaped end 66 to facilitate shallow penetration into the wall of the heart by spreading the heart wall tissue. The remaining portion 67 of penetrating tip 65 extending from conical-shaped end 66 has a cylindrical configuration. A series of deflectable barbs 68 protrude radially around the surface of cylindrical portion 67. Barbs 68 essentially act as gripping members to engage with the heart wall and securely hold marker 60 in place until removal is desired. Upon a sufficient force pulling marker 60 away from the heart wall, barbs 68 relatively easily disengage from heart wall to free marker 60.

Penetrating tip 65 preferably is constructed from PEEK, or other suitable biocompatible material, such as, for example, polyimide, polyamide, acetal, urethane, or polyester, and has a length less than the thickness of the heart wall and preferably of approximately 0.156 inches, and a diameter preferably of approximately 0.030 inches. Barbs 68 preferably extend from cylindrical portion 67 of penetrating tip 65 at angles ranging from approximately 10 degrees to approximately 45 degrees, and have respective lengths of 0.005 inches measured from the outer surface of cylindrical portion 67.

A suture line 70 attaches to a proximal end of penetrating tip 65. Suture line 70 can either be formed by necking and drawing the back end of penetrating tip 65 or can be a standard suture material secured directly to penetrating tip 65 by, for example, a knot. Such a standard suture material includes 3-0 polyester, but other materials known in the art also may be utilized. Suture line 70 has a length of approximately 2 to 14 inches, thus allowing the marker to be seen more readily, as well as enabling a surgeon to locate the marker through tactile sensation.

In a preferred form of the invention, the preloading of marker 60 into tube 51 is preferably performed at a factory prior to implantation, with a number of marker-preloaded tubes 51 being supplied for the splint implantation procedure. Most preferably, 6 preloaded tubes 51 will be supplied for an implantation procedure to deliver six markers corresponding to the intersection points of each of three splint assemblies implanted into the heart, as shown in FIG. 14. After each marker 60 is delivered, tube 51 is removed from probe/marking device 50 and disposed of as appropriate. A new preloaded tube 51 is thereafter inserted for delivery of the next marker 60.

Thus, the locating and marking procedure can be repeated at each splint assembly positioning location on both sides of the heart chamber in the manner described above. The various splint assemblies are then delivered to each of the locations of the heart indicated by each of the delivered markers. The markers are removed once delivery of the splint assembly is complete.

Various delivery techniques have been described in prior applications, such as U.S. patent application Ser. No. 09/123,977, filed on Jul. 29, 1998, and entitled "Transventricular Implant Tools and Devices," the entire disclosure of which is incorporated herein by reference. Briefly, the delivery of a splint assembly proceeds in the following manner: Once markers have been delivered to heart wall on both sides of the chamber, an alignment clamp is positioned around the heart at those locations. The alignment clamp includes a guide tube, through which a needle is first delivered at the marker locations to penetrate the heart wall. The needle is extended transverse the heart such that each end of the needle penetrates locations on the heart wall corresponding to the ends of the splint assembly to be implanted. The needle defines a lumen extending along its length, through which leader tube 5 and tension member 2 are inserted via the guide tube in the alignment clamp. Once leader tube 5 extends through the second marker location, it can be pulled which in turn pulls tension member 2 across the heart wall. Leader tube 5 should be pulled until fixed pad assembly 3 engages the exterior surface of the heart wall. The needle can then be removed from the heart by pulling it off the free end of leader tube 5. Similarly, markers 60 also can be removed from the heart wall, either before or after removing the needle.

Next, leader tube 5 is fed into a measuring and tightening device, which also has been described previously in U.S. application Ser. No. 09/123,977. Essentially stop band 7 on leader tube 5 engages with the measuring and tightening device, and leader tube 5 can be pulled a predetermined distance to tighten tension member 2 to a desired length between fixed pad assembly 3 and adjustable pad assembly 4. Stop band 7 is originally affixed to leader tube 5 at a known distance from fixed pad assembly 3. Thus, upon engagement of stop band 7 with the measuring and tightening device, it may be determined how much to pull leader tube 5 to adjust the length of tension member 2 that will extend between the two pad assemblies. Stop band 7 serves as a marker to align with a measurement scale on the measuring and tightening device.

Once tension member 2 has been adjusted to the desired length, adjustable pad assembly 4, previously fed onto leader tube 5 and tension member 2, is secured to tension member 2 adjacent the exterior of the heart wall in the manner described above with reference to the description of FIGS. 5–9

Although preferably three splint assemblies are placed with respect to the heart, the methods described above to place the splint assemblies with respect to the heart can be repeated for other desired numbers of splint assemblies to achieve a particular configuration. The length of the tension members extending between the fixed and adjustable pad assemblies also can be optimally determined based upon the size and condition of the patient's heart. It should also be noted that although the left ventricle has been referred to here for illustrative purposes, the apparatus and methods of this invention can be used to splint multiple chambers of a patient's heart, including the right ventricle or either atrium.

Furthermore, the alignments shown in FIGS. 13 and 14 are illustrative only and may be shifted or rotated about a vertical axis generally disposed through the left ventricle and still avoid the major coronay vessels and papillary muscles.

In addition, the inventive device and methods can be implanted to treat a heart having aneurysms or infarcted regions similar to those described in prior U.S. application Ser. No. 09/422,328 discussed earlier herein.

Other mechanisms for locating and marking the positions on the heart wall through which to implant the splint assemblies are also within the scope of the present invention. Several of these techniques have been described in prior U.S. application Ser. No. 09/123,977, filed Jul. 29, 1998.

The various components of the splint assembly to be implanted in the heart should be made of biocompatible material that can remain in the human body indefinitely. Any surface engaging portions of the heart should be atraumatic in order to avoid tissue damage.

It will be understood that this disclosure, in many respects, is only illustrative. Changes may be made in details, particularly in matters of shape, size, material, number and arrangement of parts without exceeding the scope of the invention. Accordingly, the scope of the invention is as defined in the language of the appended claims.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An apparatus for improving cardiac function, comprising:
   an elongate member configured to extend transverse a heart chamber;
   a first heart-engaging assembly attached to the elongate member and configured to engage a first exterior location of a heart wall;
   a second heart-engaging assembly configured to be secured onto the elongate member and to engage a second exterior location of the heart wall; and a fixation member configured to penetrate the elongate member to thereby hold at least one of the first heart-engaging assembly and the second heart-engaging assembly in a fixed position along the elongate member.

2. The apparatus of claim 1, wherein the second heart-engaging assembly is configured to be slidably positioned along the elongate member prior to securement to the elongate member such that a length of the elongate member between the first and second heart-engaging assemblies can be adjusted during placement of the elongate member transverse the heart chamber.

3. The apparatus of claim 1, wherein the first heart-engaging assembly is fixedly attached to the elongate member.

4. The apparatus of claim 1, wherein surfaces of the first and second heart-engaging assemblies engaging the heart wall have substantially convex configurations relative to the heart wall.

5. The apparatus of claim 1, wherein the elongate member extends through apertures defined by each of the first and second heart-engaging assemblies.

6. The apparatus of claim 1, wherein each of the first and second heart-engaging assemblies has a substantially disk-like shape.

7. The apparatus of claim 6, wherein each of the first and second heart-engaging assemblies has a diameter of approximately 1.9 cm.

8. The apparatus of claim 1, wherein each of the first and second heart-engaging assemblies is made of a rigid thermoplastic material.

9. The apparatus of claim 1, wherein each of the first and second heart-engaging assemblies includes a covering made of a material facilitating tissue ingrowth.

10. The apparatus of claim 1, wherein the first heart-engaging assembly includes the fixation member and the fixation member is configured to engage the elongate member to attach the elongate member to the first heart-engaging assembly.

11. The apparatus of claim 10, wherein the elongate member and the fixation member extend substantially perpendicular to each other.

12. The apparatus of claim 11, wherein the elongate member folds within a portion of the first heart-engaging assembly such that the fixation member engages the elongate member in two locations.

13. The apparatus of claim 12, wherein the first heart-engaging assembly includes a channel for receiving the fixation member.

14. The apparatus of claim 10, wherein the fixation member includes a sharpened pin.

15. The apparatus of claim 10, wherein two fixation members extend substantially parallel to each other and perpendicular to the elongate member to attach the first heart-engaging assembly to the elongate member.

16. The apparatus of claim 1, wherein the second heart-engaging assembly is configured to be selectively secured along a length of the elongate member.

17. The apparatus of claim 1, wherein the second heart-engaging assembly includes the fixation member to secure the second heart-engaging assembly to the elongate member.

18. The apparatus of claim 17, wherein the fixation member is actuatable.

19. The apparatus of claim 18, wherein prior to actuation of the fixation member, the second heart-engaging assembly is movable relative to a length of the elongate member.

20. The apparatus of claim 18, wherein the second heart-engaging assembly includes a channel along which the actuatable fixation member advances to penetrate the elongate member.

21. The apparatus of claim 18, wherein the second heart engaging assembly is configured to engage with an actuator to actuate the fixation member.

22. The apparatus of claim 17, wherein the fixation member includes a staple.

23. The apparatus of claim 18, wherein the second heart-engaging assembly includes a safety mechanism to prevent the actuatable fixation member from advancing prior to actuation and from disengaging from the elongate member after penetration thereof.

24. The apparatus of claim 1, wherein the fixation member includes a first fixation member and a second fixation member, the first fixation member configured to penetrate the elongate member and hold the first heart-engaging assembly in a fixed position along a length of the elongate member, and the second fixation member configured to penetrate the elongate member and hold the second heart-engaging assembly in a fixed position along the length of the elongate member.

25. The apparatus of claim 24, wherein the second fixation member is actuatable to selectively secure the second heart-engaging assembly along the length of the elongate member during placement of the elongate member transverse the heart chamber.

* * * * *